(12) United States Patent
Carpentier et al.

(10) Patent No.: US 9,133,304 B2
(45) Date of Patent: Sep. 15, 2015

(54) PROCESS FOR IMMORTAL RING-OPENING POLYMERISATION OF CYCLIC ESTERS AND CYCLIC CARBONATES

(71) Applicants: TOTAL RESEARCH & TECHNOLOGY FELUY, Seneffe (Feluy) (BE); CENTRE NATIONAL DE LA RECHERCHE SCIENTIFIQUE (CNRS), Paris (FR)

(72) Inventors: Jean-Francois Carpentier, Acigne (FR); Yann Sarazin, Rennes (FR); Valentin Poirier, Rennes (FR); Marion Helou, Brussels (BE)

(73) Assignees: TOTAL RESEARCH & TECHNOLOGY FELUY, Seneffe (Feluy) (BE); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 0 days.

(21) Appl. No.: 14/553,283

(22) Filed: Nov. 25, 2014

(65) Prior Publication Data
US 2015/0148516 A1 May 28, 2015

Related U.S. Application Data

(62) Division of application No. 13/265,980, filed as application No. PCT/EP2010/055794 on Apr. 29, 2010.

(30) Foreign Application Priority Data

Apr. 30, 2009 (EP) .................................... 09290318

(51) Int. Cl.
| | |
|---|---|
| *C08G 63/84* | (2006.01) |
| *C08G 63/85* | (2006.01) |
| *C08G 63/08* | (2006.01) |
| *C08G 64/16* | (2006.01) |
| *C08G 63/83* | (2006.01) |
| *C08G 63/82* | (2006.01) |
| *C08G 64/30* | (2006.01) |

(52) U.S. Cl.
CPC ................ *C08G 63/85* (2013.01); *C08G 63/08* (2013.01); *C08G 63/823* (2013.01); *C08G 63/83* (2013.01); *C08G 64/1608* (2013.01); *C08G 64/30* (2013.01)

(58) Field of Classification Search
CPC ................................. C08G 63/08; C08G 63/64
USPC ........................... 525/413, 415; 528/354, 357
See application file for complete search history.

(56) References Cited

FOREIGN PATENT DOCUMENTS

FR EP 2151457 * 2/2010

OTHER PUBLICATIONS

C. J. Hawker, et al., "Initiating Systems for Nitroxide-Mediated "Living" Free Radical Polymerizations: Synthesis and Evaluation"; Macromolecules; vol. 29, No. 16, Jul. 29, 1996, pp. 5245-5254.

* cited by examiner

*Primary Examiner* — Gregory Listvoyb

(57) ABSTRACT

The present invention discloses new catalyst systems based on complexes of divalent metals supported by chelating phenoxy ligands for immortal ring-opening polymerization of cyclic esters and cyclic carbonates.

20 Claims, 13 Drawing Sheets

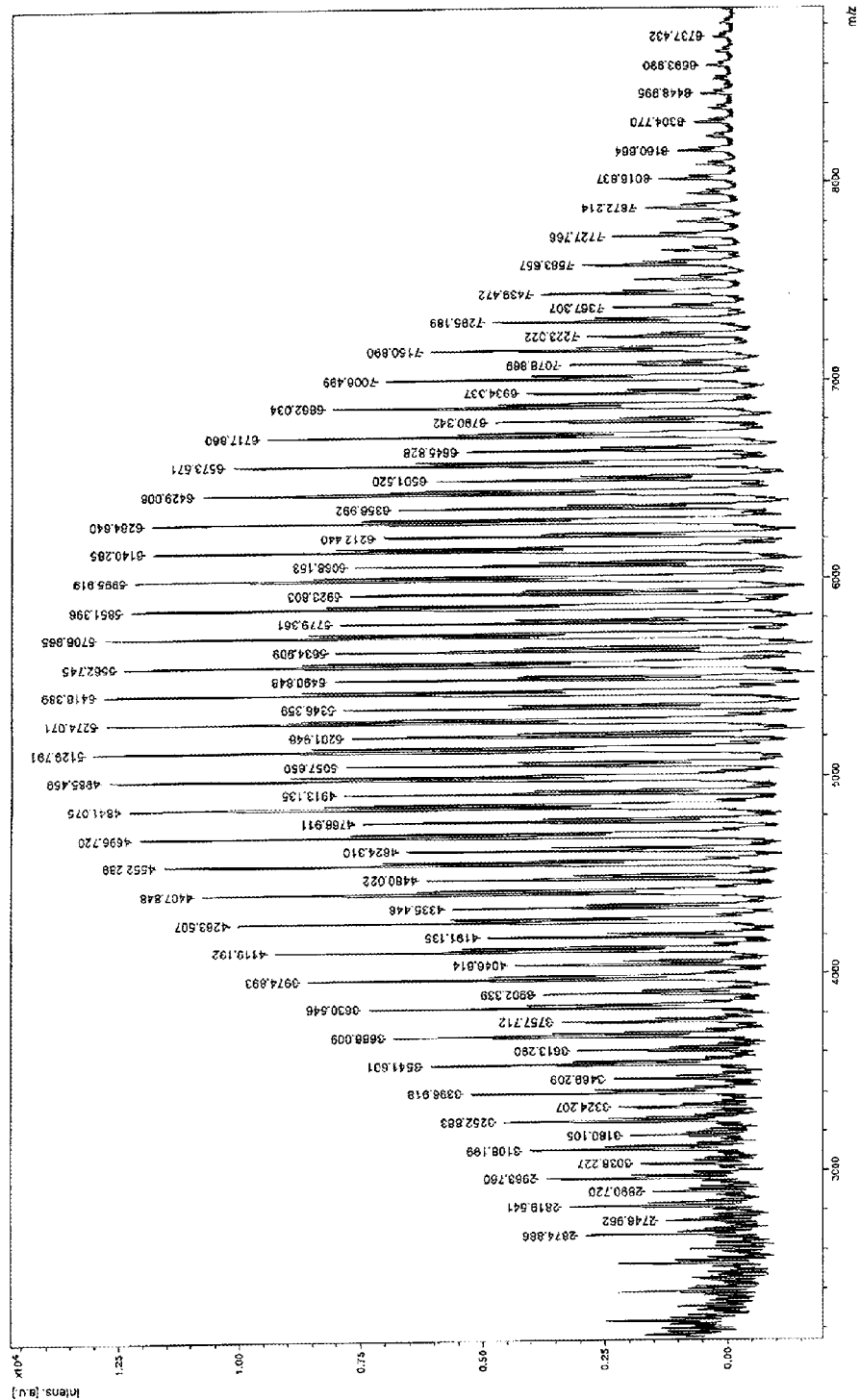

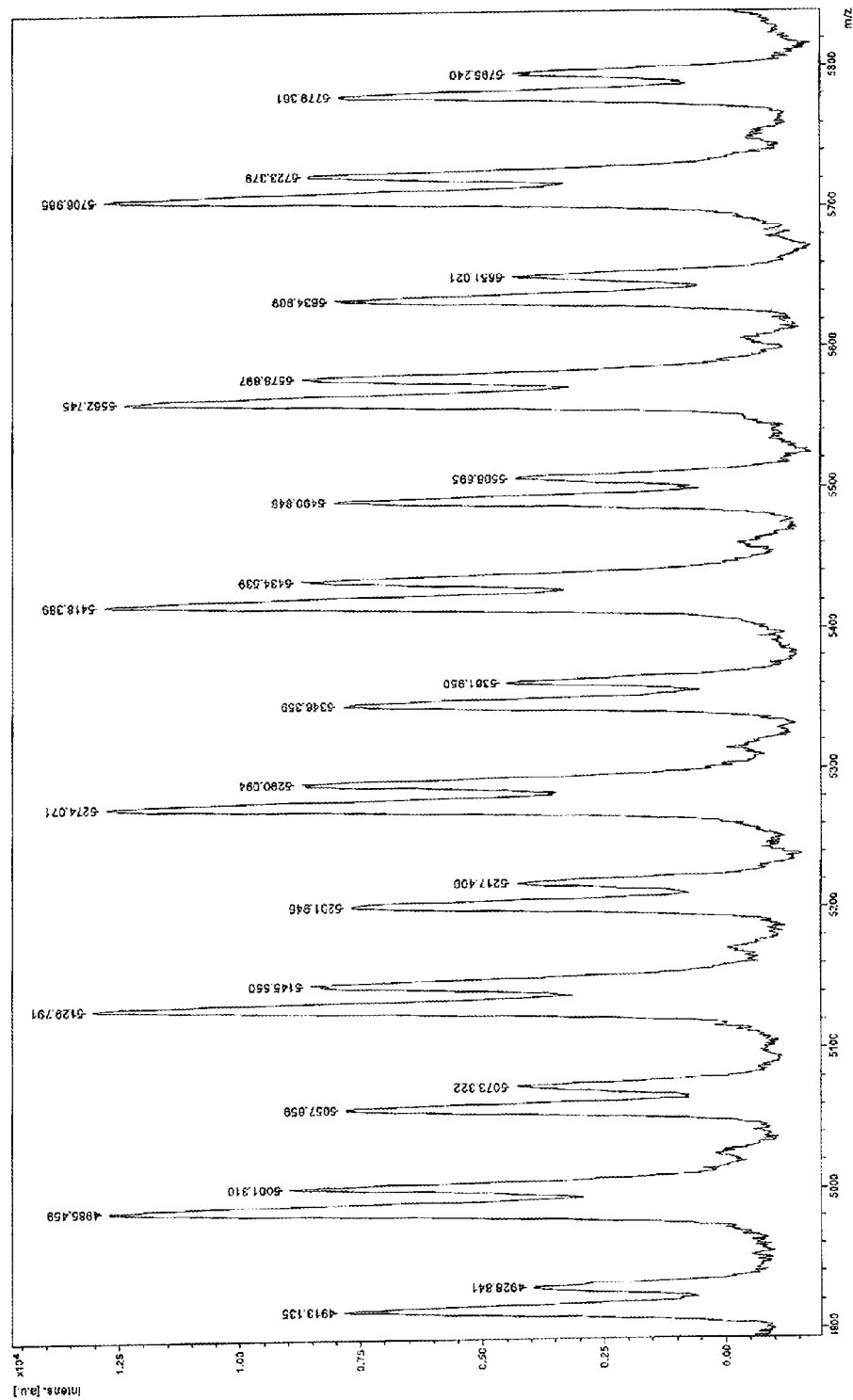

PROCESS FOR IMMORTAL RING-OPENING POLYMERISATION OF CYCLIC ESTERS AND CYCLIC CARBONATES

CROSS REFERENCE TO RELATED APPLICATIONS

This application is a Divisional of U.S. patent application Ser. No. 13/265,980, filed on Jan. 13, 2012, which is a national stage entry of PCT/EP2010/055794, filed on Apr. 29, 2010, which claims priority from European Application No. 09290318.6, filed on Apr. 30, 2009.

The present invention discloses new catalyst systems based on complexes of divalent metals supported by chelating phenoxy ligands for immortal ring-opening polymerisation of cyclic esters and cyclic carbonates.

Growing concern towards the possible depletion of fossil feedstocks necessary for the production of most commodity polymers, combined with the instability of the prices of crude oil and more generally an ever-increasing consideration towards environmental issues have prompted both industrial and academic research groups to investigate the use of bio-friendly polymers as a substitute to the already existing synthetic materials. As a consequence, the past ten years have witnessed a surge of interest in the fields of polymerisation of bio-resourced monomers and preparation of synthetic, biodegradable polymers.

Ring-opening polymerisation (ROP) of cyclic esters has emerged as the most convenient way to generate bio-degradable aliphatic polyesters as described for example in Uhrich et al. (K. E. Uhrich, S. M. Cannizzaro, R. S. Langer, K. M. Shakesheff, Chem. Rev., 1999, 99, 3181-3198), or in Ikada and Tsuji (Y. Ikada, H. Tsuji, Macromol. Rapid. Commun., 2000, 21, 117-132) or in Langer (R. Langer, Acc. Chem. Res., 2000, 33, 94-101) or in Okada (M. Okada, Prog. Polym. Sci., 2002, 27, 87-133).

The emphasis was initially placed on the (co)polymerisation of ε-caprolactone (CL) and glycolide (GL) to generate polymers suitable for applications in the biomedical field as disclosed for example in Vert (M. Vert, Biomacromolecules 2005, 6, 538-546) or in Albertsson and Varma (A.-C. Albertsson, I. K. Varma, Biomacromolecules 2003, 4, 1466-1486) or in Sudesh et al. (K. Sudesh, H. Abe, Y. Doi Prog. Polym. Sci. 2000, 25, 1503-1555) or in Nair and Laurence (L. S. Nair, C. T. Laurence, Prog. Polym. Sci. 2007, 32, 762-798).

Many research groups have however recently shifted their attention towards the polymerisation of cyclic di-ester derived from lactic acid and more particularly to the polymerisation of lactide (LA) as described for example in Mecking (S. Mecking, Angew. Chem. Int. Ed., 2004, 43, 1078-1085) or in Dechy-Cabaret et al. (O. Dechy-Cabaret, B. Martin-Vaca, D. Bourissou, Chem. Rev., 2004, 104, 6147-6176). LA is a bio-renewable resource, which can be produced by fermentation of sugar-roots and corn. Tin-based initiators, based typically on tin(II) 2-ethyl-hexanoate, are commonly used in industry for the ROP of LA and other cyclic monomers. These systems are slow, poorly controlled and present serious issues related to the heavy tin element, as discussed for example in Drumright et al. (R. E. Drumright, P. R. Gruber, D. E. Henton, Adv. Mater., 2000, 12, 1841-1846) or in Okada (M. Okada, Prog. Polym. Sci., 2002, 27, 87-133).

Recently, several well-defined metallic initiators have been developed for the controlled, living ROP of the various isomers of LA such as rac-, S,S- and R,R-LA as disclosed for example in O'Keefe et al. (B. J. O'Keefe, M. A. Hillmyer, W. B. Tolman, J. Chem. Soc., Dalton Trans., 2001, 2215-2224), or in Lou et al. (Lou, C. Detrembleur, R. Jérôme, Macromol. Rapid. Commun., 2003, 24, 161-172), or in Nakano et al. (K. Nakano, N. Kosaka, T. Hiyama, K. Nozaki, J. Chem. Soc., Dalton Trans., 2003, 4039-4050), or in Dechy-Cabaret et al. (O. Dechy-Cabaret, B. Martin-Vaca, D. Bourissou, Chem. Rev., 2004, 104, 6147-6176), or in Wu et al. (Wu, T.-L Yu, C.-T. Chen, C.-C. Lin, Coord. Chem. Rev., 2006, 250, 602-626), or in Amgoune et al. (Amgoune, C. M. Thomas, J.-F. Carpentier, Pure Appl. Chem. 2007, 79, 2013-2030).

They are based mostly on:

non-toxic zinc (M. Cheng, A. B. Attygalle, E. B. Lobkovsky, G. W. Coates, J. Am. Chem. Soc., 1999, 121, 11583-11584; B. M. Chamberlain, M. Cheng, D. R. Moore, T. M. Ovitt, E. B. Lobkovsky, G. W. Coates, J. Am. Chem. Soc., 2001, 123, 3229-3238; C. K. Williams, L. E. Breyfogle, S. K. Choi, W. Nam, V. G. Young Jr., M. A. Hillmyer, W. B. Tolman, J. Am. Chem. Soc., 2003, 125, 11350-11359; G. Labourdette, D. J. Lee, B. O. Patrick, M. B. Ezhova, P. Mehrkhodavandi, Organometallics, 2009, 28, 1309-1319; Z. Zheng, G. Zhao, R. Fablet, M. Bouyahyi, C. M. Thomas, T. Roisnel, O. Casagrande Jr., J.-F. Carpentier, New J. Chem., 2008, 32, 2279-2291), aluminium (N. Spassky, M. Wisniewski, C. Pluta, A. LeBorgne, Macromol. Chem. Phys., 1996, 197, 2627-2637; T. M. Ovitt, G. W. Coates, J. Am. Chem. Soc., 1999, 121, 4072-4073; M. Ovitt, G. W. Coates, J. Am. Chem. Soc., 2002, 124, 1316-1326; N. Nomura, R. Ishii, Y. Yamamoto, T. Kondo, Chem. Eur. J., 2007, 13, 4433-4451; H. Zhu, E. Y.-X. Chen, Organometallics, 2007, 26, 5395-5405) or group 3 metals and lanthanides (C.-X. Cai, A. Amgoune, C. W. Lehmann, J.-F. Carpentier, Chem. Commun., 2004, 330-331; A. Amgoune, C. M. Thomas, T. Roisnel, J.-F. Carpentier, Chem. Eur. J., 2006, 12, 169-179; A. Amgoune, C. M. Thomas, S. Ilinca, T. Roisnel, J.-F. Carpentier, Angew. Chem. Int. Ed., 2006, 45, 2782-2784).

Some of these single-site complexes are also efficient for the ROP of β-butyrolactone (BBL), producing poly(3-hydroxybutyrate)s, a naturally-occurring highly crystalline thermoplastic resin produced by several algae and bacteria as their isotactic stereoisomer, some catalyst systems leading to syndiotactic polymers as discussed by Amgoume et al. A. (Amgoune, C. M. Thomas, S. Vince, T. Roisnel, J.-F. Carpentier, Angew. Chem. Int. Ed., 2006, 45, 2782-2784), or by Rieth et al. (L. R. Rieth, D. R. Moore, E. B. Lobkovsky, G. W. Coates, J. Am. Chem. Soc., 2002, 124, 15239-15248) or by Ajellal et al. (N. Ajellal, D. M. Lyubov, M. A. Sinenkov, G. K. Fukin, A. V. Cherkasov, C. M. Thomas, J.-F. Carpentier, A. A. Trifonov, Chem. Eur. J., 2008, 14, 5440-5448) or by Ajellal et al. (N. Ajellal, M. Bouyahyi, A. Amgoune, C. M. Thomas, A. Bondon, I. Pillin, Y. Grohens, J.-F. Carpentier, Macromolecules, 2009, 42, 987-993).

The ROP of trimethylene carbonate (TMC) has also started to attract considerable attention in the past 3 years as disclosed in S. Matsumura Adv. Polym. Sci. 2005, 194, 95-132, or in Hellaye et al. (M. Le Hellaye, N. Fortin, J. Guilloteau, A. Soum, S. Lecommandoux, S. M. Guillaume Biomacromolecules, 2008, 9, 1924-1933) or in Darensbourg et al. (D. J. Darensbourg, W. Choi, P. Ganguly, C. P. Richers Macromolecules, 2006, 39, 4374-4379) or in Helou et al. (M. Helou, O. Miserque, J.-M. Brusson, J.-F. Carpentier, S. M. Guillaume, Chem. Eur. J., 2008, 14, 8772-8775) or in European patent application no 08290187.7. TMC is a bio-resourced monomer directly derived from glycerol, itself a by-product of the degradation of triglycerides.

This molecule, unlike LA, is not issued from the exploitation of resources otherwise used in the food chain as discussed by Zhou et al. (C.-H. Zhou, J. N. Beltramini, Y.-X. Fan, G. Q. Lu *Chem. Soc. Rev,* 2008, 37, 527-549) or by Behr et al. (A. Behr, J. Eilting, K. Irawadi, J. Leschinski, F. Lindner *Green Chem.* 2008, 10, 13-30).

In addition to the metal-based systems, one must mention the results of Kamber et al. (N. E. Kamber, W. Jeong, R. M. Waymouth, R. C. Pratt, B. G. G. Lohmeijer, J. L. Hedrick, *Chem. Rev.,* 2007, 107, 5813-5840 and Bourissou et al. (D. Bourissou, S. Moebs-Sanchez, B. Martín-Vaca, C. R. *Chimie,* 2007, 10, 775-794) who have pioneered the development of organic catalysts for the controlled ROP of these cyclic monomers.

Significant advances have been achieved in the ROP of these monomers, most notably with respect to the control of the stereochemistry in the case of monomers such as LA and BBL which contain one or more stereo-centres and with respect to the molecular weight of the resulting polyesters and polycarbonates. The fact that these systems are generally "living" precluded, however, their use for industrial purposes. Indeed, they were able to generate only a single polymer chain per active centre, and could only transform a small quantity of monomer, typically 100-2 000 equivalents, per active site. Industrial catalytic systems must be very productive: they must be able to polymerise several thousands of equivalents of monomer to yield hundreds of polymer chains per active centre. One way to reliably achieve such goal in the field of ROP was to operate chain transfer during the course of a so-called "immortal" living polymerisation, thanks to the addition of a chain-transfer agent as described for example in European patent application no 08290187.7 or in Asano et al. (S. Asano, T. Aida, S. Inoue, *J. Chem. Soc., Chem. Commun.,* 1985, 1148-1149) or in Aida et al. (T. Aida, Y. Maekawa, S. Asano, S. Inoue, *Macromolecules,* 1988, 21, 1195-1202) or in Aida and Inoue (T. Aida, S. Inoue, *Acc. Chem. Res.,* 1996, 29, 39-48) or in Martin et al. (E. Martin, P. Dubois, R. Jérôme, *Macromolecules,* 2000, 33, 1530-1535) or in Amgoume et al. (A. Amgoune, C. M. Thomas, J.-F. Carpentier, *Macromol. Rapid. Commun.,* 2007, 28, 693-697). For instance, European patent application no 08290187.7 disclosed that the binary system (BDI)ZnN(SiMe$_3$)$_2$/Bn-OH wherein BDI=(2,6-$^i$Pr$_2$-C$_6$H$_3$)N=C(Me)-CH=C(Me)-N(2,6-$^i$Pr$_2$-C$_6$H$_3$) and Bn-=C$_6$H$_5$CH$_2$— could be employed with great efficiency for the ROP of TMC, allowing the controlled polymerisation of up to 50 000 equivalents of TMC in presence of 50 equivalents of benzyl alcohol. The method used from 20 to 100 ppm of metal catalyst, thus minimising metal residues in the final polymers. In addition, the catalyst system was based on zinc, a "bio-metal", which was not associated to potential toxicity issues contrary to tin-based systems.

In addition, another challenge consists in the incorporation of sizeable amounts of bio-resources in the classical commodity synthetic polymers, namely poly($\alpha$-olefin)s and more particularly poly(styrene)s. The preparation of copolymers of cyclic esters (LA, CL, GL) or carbonates (TMC) with styrene (S) has therefore been investigated for example in European patent application no 08290732.0, or in Zalusky et al. (A. S. Zalusky, R. Olayo-Valles, J. H. Wolf, M. A. Hillmyer, *J. Am. Chem. Soc.,* 2002, 124, 12761-12773) or in Barakat et al. (I. Barakat, P. Dubois, R. Jérôme, P. Teyssié, *J. Pol. Sci. Part A: Polym. Chem.,* 1993, 31, 505-514, L. Barakat, P. Dubois, R. Jérôme, P. Teyssié, E. Goethals, *J. Pol. Sci. Part A: Polym. Chem.,* 1994, 32, 2099-2110; I. Barakat, P. Dubois, C. Grandfils, R. Jérôme, *J. Pol. Sci. Part A: Polym. Chem.,* 1999, 37, 2401-2411) or in Furch et al. (M. Furch, J. L. Eguiburu, M. J. Fernandez-Berridi, J. San Román, *Polymer,* 1998, 39, 1977-1982) or in Eguiburu et al. (J. L. Eguiburu, M. J. Fernandez-Berridi, F. P. Cossio, J. San Román, *Macromolecules,* 1999, 32, 8252-8258; J. L. Eguiburu, M. J. Fernandez-Berridi, J. San Román, *Polymer,* 2000, 41, 6439-6445), or in Qiu et al. (H. Qiu, J. Rieger, B. Gilbert, R. Jérôme, C. Jérôme, *Chem. Mater.,* 2004, 18, 850-856), or in Kricheldorf et al. (H. R. Kricheldorf, S.-R. Lee, S. Bush, *Macromolecules,* 1996, 29, 1375-1381), or in Trollsås et al. (M. Trollsås, C. J. Hawker, J. L. Hedrick, G. Carrot, J. Hilborn, *Macromolecules,* 1998, 31, 5960-5963), or in Hawker et al. (C. J. Hawker, D. Mecerreyes, E. Elce, J. Dao, J. L. Hedrick, I. Bakarat, P. Dubois, R. Jérôme, W. Volsken, *Macromol. Chem. Phys.,* 1997, 198, 155-166), or in Yoshida and Osagawa (E. Yoshida, Y. Osagawa, *Macromolecules,* 1998, 31, 1446-1453), or in Wang et al. (Y. Wang, G. Lu, J. Huang, *J. Pol. Sci. Part A: Polym. Chem.,* 2004, 42, 2093-2099), or in Dubois et al. (P. Dubois, R. Jérôme, P. Teyssié, *Macromolecules,* 1991, 24, 977-981), or in Jabbar et al. (R. Jabbar, A. Graffe, B. Lessard, M. Marić, *J. Pol. Sci. Part A: Polym. Chem.,* 2008, 109, 3185-3195).

LA and TMC have been used to prepare copolymers of styrene with physical and mechanical properties related to those of polystyrenes, said copolymers containing up to 50% of the bio-monomer.

European patent application no 08290732.0 discloses the immortal polymerisation of large amounts of LA. It was performed in neat styrene with safe metal-based initiators such as (BDI)ZnN(SiMe$_3$)$_2$ in combination with a bi-functional alcohol such as 4-hydroxy-2,2,6,6-tetramethylpiperidinooxy (TEMPO-OH) or 2-hydroxyethyl-methacrylate (HEMA), to produce end-functionalised polylactides. These PLAs were then employed for the controlled preparation of poly(lactide-block-styrene)s wherein the length of each block could be tuned at will.

There is however large space left for improvement.

It is an objective of the present invention to prepare new phenoxy-based ligands.

It is another objective of the present invention to use these phenoxy-based ligands for preparing divalent metal complexes.

It is also an objective of the present invention to use the metallic complexes in catalytic systems for the controlled immortal ROP of cyclic esters and cyclic carbonates.

It is a further objective of the present invention to prepare end-functionalised PLAs.

It is yet a further objective of the present invention to promote in situ-synthesis of copolymers of lactide and styrene.

Any one of those aims is, at least partially, fulfilled by the present invention.

Accordingly, the present invention discloses a class of phenol-based pro-ligands of formula

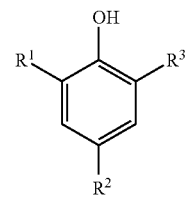

wherein
R¹ is

wherein m is 1, 2 or 3 and n≥1);

R² is hydrocarbyl group having 1 to 10 carbon atoms and is preferably selected from methyl, ethyl, iso-propyl, tert-butyl or neo-pentyl;

R³ is the same as R¹ or is hydrocarbyl group having 1 to 20 carbon atoms and is preferably alkyl selected from methyl, ethyl, iso-propyl, tert-butyl, neo-pentyl, cumyl, trityl or aryl selected from phenyl, 2,4,6-trimethylphenyl, 2,6-diisopropylphenyl.

The key element in the substitution pattern is R¹ which must simultaneously comprise a nitrogen function and an oxygen atom engaged in the cycle. It is a cycloazoether.

The present ligands are particularly stable because of the presence of oxygen in the morpholine or aza-ethers. Ligands of the prior art such as for examples those disclosed in Zheng et al. (Z. Zheng, G. Zhao, R. Fablet, M. Bouyahyi, C. M. Thomas, T. Roisnel, O. Casagrande, J.-F. Carpentier, in New Journal of Chemistry, 32, 2279, 2008) are less performing than the present ligands as oxygen is not present in the piperazine cycle. They are therefore less stable than the present ligands with respect to the metallic centre. The ligands of the prior art thus decompose more rapidly than the present ligands and their productivity and degree of control on the polymerisation reaction are thereby reduced.

These pro-ligands can be prepared following any method known in the art. The present method for preparing the pro-ligands and metal complexes is a modification of the method described in Schanmuga at al. (S. Shanmuga Sundara Raj, M. N. Ponnuswamy, G. Shanmugam, M. Kandaswamy, *J. Crystallogr. Spectrosc. Res.*, 1993, 23, 607-610) or in Teipel et al. (S. Teipel, K. Griesar, W, Haase, B. Krebs, *Inorg. Chem.*, 1994, 33, 456-464). The complete syntheses of ligands and the further syntheses of metal complexes can be achieved in at most 48 h to give analytically pure compounds on a multi-gram scale. For comparison, the synthesis of (BDI)ZnN (SiMe₃)₂, which is a very efficient zinc-based initiator for the ROP of LA, BBL or TMC, requires two full weeks and harsh conditions.

The pro-ligands are then used to prepare complexes of divalent metals of Groups 2 and 12 of the Periodic Table. The preferred metals are magnesium, calcium, zinc, strontium and barium, preferably magnesium, calcium and zinc. The complexes are prepared by reacting the pro-ligand with a precursor M(X)₂ wherein X is either an alkyl having from 1 to 6 carbon atoms such as for example methyl, ethyl, n-butyl, phenyl, or an amido group such as for example N(SiMe₃)₂, NMe₂, NEt₂, NiPr₂, or an alkoxide group such as for example OEt, OiPr, OtBu, OCH₂Ph, OSiPh₃.

The preferred precursors are ZnEt₂, Mg(nBu)₂, Mg(N (SiMe₃)₂)₂, Ca(N(SiMe₃)₂)₂(THF)₂.

The present invention further provides metal complexes of formula [LO]-M-X, wherein M is Zn, Mg, Ca, Sr or Ba.

X is hydrocarbyl, or alkoxide group OR" wherein R" is hydrocarbyl, aryl, silyl, or amino group NR*₂ wherein R* is SiMe₃, iso-propyl, methyl or ethyl. The preferred hydrocarbyl is ethyl.

[LO] is 2-R¹,4-R²,6-R³—C₆H₂O.

wherein R¹, R² and R³ are as described hereabove.

The present invention discloses a process for polymerising cyclic esters and five- or six- or seven-membered cyclic carbonates by ROP in the presence of a system comprising an alcohol an a divalent metal complex supported by chelating phenoxy ligands.

In the presence of 1 to 10,000 equivalents, preferably of 5 to 5000 equivalents, more preferably, 5 to 1,000 equivalents of alcohol or poly-ol, these metal complexes are very active and productive catalytic systems for the controlled immortal ROP of lactides, cyclic esters and 5- to 7-membered cyclic carbonates. The polymerisation can be carried out in solution in an organic solvent or in melt, in the absence of solvent, at temperature ranging from 20° C. to 200° C., preferably from 25° C. to 110° C. Typically, the conversion of at least 50 000 and up to 500 000 equivalents of monomer, preferably 50 000 to 100 000 equivalents, can be achieved in the presence of up to thousands equivalents of alcohol per metal centre.

The alcohol can be represented by formula R'OH wherein R' is an hydrocarbyl group, linear or branched, having from 1 to 20 carbon atoms. Preferably R' is a primary or secondary alkyl residue or benzylic group, more preferably it is iso-propyl (iPr) or benzyl (Bn). It can also be a poly-ol such as a diol, triol or higher functionality polyhydridic alcohol, typically selected from 1,3-propanediol or trimethylolpropane, possibly derived from biomass such as glycerol or any other sugar-based alcohol such as for example erythritol or a cyclodextrine. All alcohols can be used individually or in combination.

More preferably the alcohol is selected from iso-propanol, sec-butanol or benzyl alcohol.

The polymerisation reaction can be represented by:

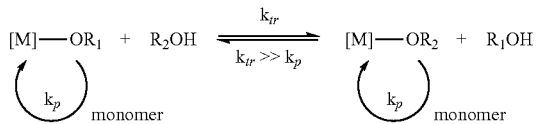

R₁, R₂ = growing polymer chain; [M]: organometallic fragment
k$_{tr}$: transfer rate constant; k$_p$: propagation rate constant In the present polymerisation scheme, the alcohol acts as a reversible transfer agent. During chain propagation, a rapid alkoxide/alcohol exchange takes place. It is observed that, as the ratio alcohol/metal increases, the molecular weight of the polymer chains decreases to the same extent.

If the rate of transfer reaction k$_{tr}$ is rapid enough relative to the polymerisation rate k$_p$, the molar mass distribution of the macromolecules formed is narrow.

At a constant alcohol/metal ratio, the molecular weight of the polycarbonate depends upon the nature of the alcohol/polyol.

Additionally, functionalised alcohols can be used in combination with the initiators according to the present invention to promote efficiently the immortal ROP of L-LA and rac-LA and TMC in styrene thereby allowing the preparation of end-functionalised polymers. The functionalised group can in turn be used for the in situ-synthesis of copolymers of LA or TMC and styrene.

For this purpose, the preferred functionalised alcohols are preferably selected from TEMPO-OH, HEMA or various hydroxy-alkoxyamines such as AA-OH.

Preferably, the cyclic esters are selected from L-lactide (L-LA), rac-lactide, (rac-LA), or rac-β-butyrolactone, (rac-BBL).

The preferred cyclic carbonates are selected from TMC and its substituted derivatives. Non-limitative examples are shown below:

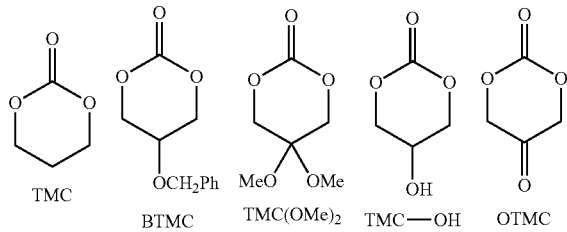

TMC    BTMC    TMC(OMe)$_2$    TMC—OH    OTMC

Polymerisation is conducted at a temperature ranging from 20° C. to 200° C., preferably between 25 and 110° C. The pressure ranges from 0.5 to 20 atm, preferably it is 1 atm.

The polymers thus prepared show typically a unimodal molecular weight distribution that ranges from 1.1 to 5.0, more typically from 1.1 to 1.7.

The number average molecular weight $M_n$ can be tuned by the monomer-to-alcohol ratio and ranges from 1 000 to 1 000 000 g/mol, more typically from 10 000 to 250 000 g/mol. In addition, the experimental molecular weights, as determined by size exclusion chromatography, are in excellent agreement with molecular weights calculated from the monomer-to-alcohol ratio and monomer conversion.

BRIEF DESCRIPTION OF THE DRAWINGS

FIGS. 7A and 7B represent the MALDI-TOF mass spectrum (main population, Na$^+$; minor population, K$^+$) of a low molecular weight PLLA having a number average molecular weight $\overline{Mn}_{GPC}$ of 4 600 g/mol prepared with L-LA/[LO$^1$]MgBu/iPrOH in relative amounts of 5 000/1/100 with a 71% conversion.

EXAMPLES

Figure 1:
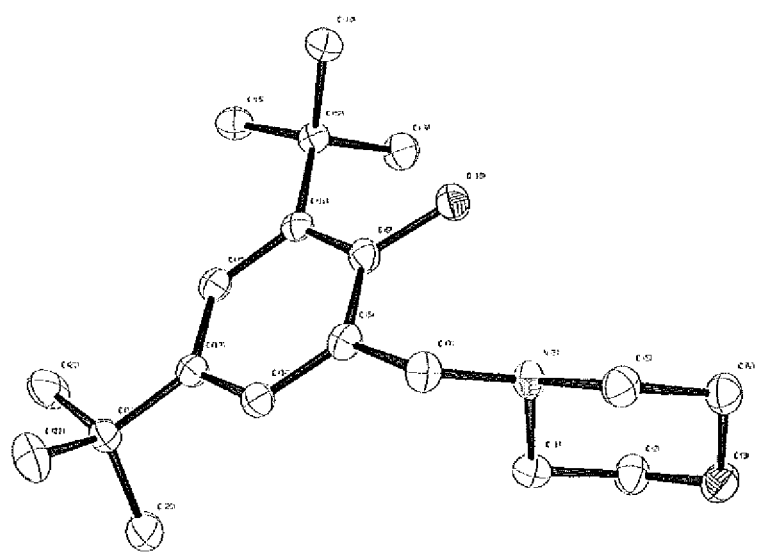
FIG. 1 represents the X-ray structure of ligand [LO$^2$]H, wherein hydrogen atoms are omitted for clarity.

All manipulations were performed under inert atmosphere on the bench using a Schlenk line and standard Schlenk techniques or in a dry, solvent-free glove-box (Jacomex; O$_2$<1 ppm, H$_2$O<5 ppm) for catalyst loading.

1-(Benzyloxy)-2-phenyl-2-(2',2',6',6'-tetramethyl-1'-piperidinyloxy)-ethane (AA-OH), BDI-H wherein BDI is (2,6-$^i$Pr$_2$-C$_6$H$_3$)N=C(Me)-CH=C(Me)-N(2,6-$^i$Pr$_2$-C$_6$H$_3$)] and complexes Zn[N(SiMe$_3$)$_2$]$_2$, {Mg[N(SiMe$_3$)$_2$]$_2$}$_2$, Ca[N(SiMe$_3$)$_2$]$_2$(THF)$_2$ and [BDI]ZnN(SiMe$_3$)$_2$ were prepared as described in the literature.

ZnEt$_2$ (1.0 M in hexanes) and MgBu$_2$ (1.0 M in heptane) were received from Aldrich and transferred to sealed ampoules for storage.

2,4-di-$^t$butyl-phenol (Acros, 97%), 4-$^t$butyl-phenol (Alfa Aesar, 99%), formaldehyde (Acros, 37 wt-% solution in water), morpholine (Acros, 99%) and 1-aza-15-crown-5 (Aldrich, 97%) were used directly as received from the provider.

Benzyl alcohol (>99.0%) was purchased from Aldrich, stored over activated 3 Å molecular sieves and subsequently used without further purification.

iPrOH (HPLC grade, VWR) was dried and distilled over magnesium powder and then stored over activated 3 Å molecular sieves.

The 4-hydroxy-2,2,6,6-tetramethylpiperidinooxy (TEMPO-OH) free radical (Acros, 98%) was recrystallised from a concentrated toluene solution stored at 4° C.; it was used in the dark at all times.

Styrene (99+%) was received from Aldrich, dried for several days over CaH$_2$, distilled by gentle heating at a temperature of about 45° C., under dynamic vacuum and stored at −24° C.; it was used within two weeks to avoid contamination by polystyrene.

Toluene was pre-dried over sodium, and systematically distilled under Argon from melted sodium prior to use.

THF was first pre-dried over sodium hydroxyde and distilled under Argon over CaH$_2$, and then freshly distilled a second time under Argon from sodium mirror/benzophenone prior to use.

Dioxane was distilled from sodium mirror/benzophenone.

All deuterated solvents (Euriso-top, Saclay, France) were stored in sealed ampoules over activated 3 Å molecular sieves and were thoroughly degassed by several freeze-thaw cycles prior to use.

Technical grade L-Lactide (L-LA) was provided by Total Petrochemicals; rac-lactide (rac-LA, 99%) was received from Acros. Purification of either of these isomers of lactide (LA) was typically ensured according to a three-step procedure by re-crystallisation from a hot, concentrated iPrOH solution (80° C.), followed by two subsequent re-crystallisations in hot toluene (105° C.). Where a shorter, less effective purification of L-LA was required, the monomer was simply re-crystallised once from iPrOH.

Trimethylene carbonate (TMC) was provided by Labso Chimie Fine (Blanquefort, France). Dry, crystalline TMC was obtained in three steps by stirring a concentrated THF solution of the monomer over calcium hydride for a minimum of 24 h, followed by filtration to remove CaH$_2$ and re-crystallisation at a temperature of −24° C.

After purification, both LA and TMC were stored at all times at a temperature of −30° C. under the inert atmosphere of the glove-box. Racemic β-butyrolactone (rac-BBL; TCI Europe, 97%) was purified by vacuum distillation from calcium hydride and kept over activated 3 Å molecular sieves.

NMR spectra were recorded on Bruker AC-200, AC-300 and AM-500 spectrometers. All chemicals shifts were determined using residual signals of the deuterated solvents and were calibrated versus SiMe$_4$. Assignment of the signals was carried out using 1D ($^1$H, $^{13}$C{$^1$H}) and 2D (COSY, HMBC, HMQC) NMR experiments. Coupling constants are given in Hertz.

Elemental analyses were performed on a Carlo Erba 1108 Elemental Analyser instrument at the London Metropolitan University and were the average of a minimum of two independent measurements.

Gel Permeation Chromatography (GPC) measurements were performed on a Polymer Laboratories PL-GPC 50 instrument equipped with a PLgel 5 Å MIXED-C column and a refractive index detector. The GPC column was eluted with THF at room temperature at 1 mL/min and was calibrated using 5 monodisperse polystyrene standards in the range of 580, to 380,000 g·mol$^{-1}$. According to literature recommendations, for example in M. Jalabert, C. Fraschini, R. E. Prud'homme, *J. Pol. Sci. Part A: Polym. Chem.*, 2007, 45, 1944-1955, or in M. Save, M. Schappacher, A. Soum, *Macromol. Chem. Phys.*, 2002, 203, 889-899, or in I. Palard, M. Schappacher, B. Belloncle, A. Soum, S. M. Guillaume, *Chem, Eur. J.*, 2007, 13, 1511-1521, the molecular weights of all poly(lactide)s, low, medium and high molecular weight poly(trimethylene carbonate)s determined vs. polystyrene standards were corrected by a Mark-Houwink factor of 0.58, 0.58, 0.73 and 0.88, respectively. The molecular weight of poly(3-hydroxybutyrate)s were directly given vs. poly(styrene)s equivalents.

The microstructure of poly(lactide) samples was determined by examination of the methine region in the homodecoupled $^1$H NMR spectrum of the polymers recorded at room temperature in CDCl$_3$ on a Bruker AM-500 spectrometer with concentrations in the range 1.0 to 2.0 mg/mL.

MALDI-TOF MS spectra were obtained with a Bruker Daltonic MicroFlex LT, using a nitrogen laser source (337 nm, 3 ns) in linear mode with a positive acceleration voltage of 20 kV. Samples were prepared as follow: 1 μL of a 2:1 mixture of a saturated solution of α-cyano-4-hydroxycinnamic acid (Bruker Care) in HPLC quality acetonitrile and a 0.1% solution of trifluoroacetic acid in ultrapure water was deposited on the sample plate. After total evaporation, 1 μL of a 5 to 10 mg/mL solution of the polymers in HPLC quality THF were deposited. Bruker Care Peptide Calibration Standard and Protein Calibration Standard I were used for external calibration.

Typical Polymerisation Procedure.

All manipulations were performed under inert atmosphere. In the glove box, the metal-based initiator and the purified monomer were placed at once in a large Schlenk tube. The vessel was sealed and removed from the glove box. All subsequent operations were carried out on a Schlenk line, using standard Schlenk techniques. Where needed, the required amount of dry, degassed solvent selected from toluene, THF or styrene, was added with a syringe to the Schlenk tube containing the initiator and monomer. The metallic complex was then activated by addition of an alcohol, selected from iPrOH, benzyl alcohol, HEMA, AA-OH or TEMPO-OH. It was added rapidly, the Schlenk vessel was immerged in an oil bath pre-set at the desired temperature and the polymerisation time was measured from this point. The reaction was terminated by addition of acidified MeOH (HCl, 1%) and the polymer was precipitated in methanol. It was purified by re-precipitation, using dichloromethane or THF as solvent and methanol as a non-solvent. The polymer was then dried to constant weight under dynamic vacuum of less than 10$^{-2}$ mbar.

Synthesis of Ligands.

The preparation of pro-ligands 2,6-bis(morpholinomethyl)-4-$^t$butyl-phenol ([LO$^1$]H), 2,4-di-$^t$butyl-6-(morpholinomethyl)-phenol ([LO$^2$]H) and 2,4-di-$^t$butyl-6-[(1-aza-15-crown-5)methyl]-phenol ([LO$^3$]H) is represented in scheme 1.

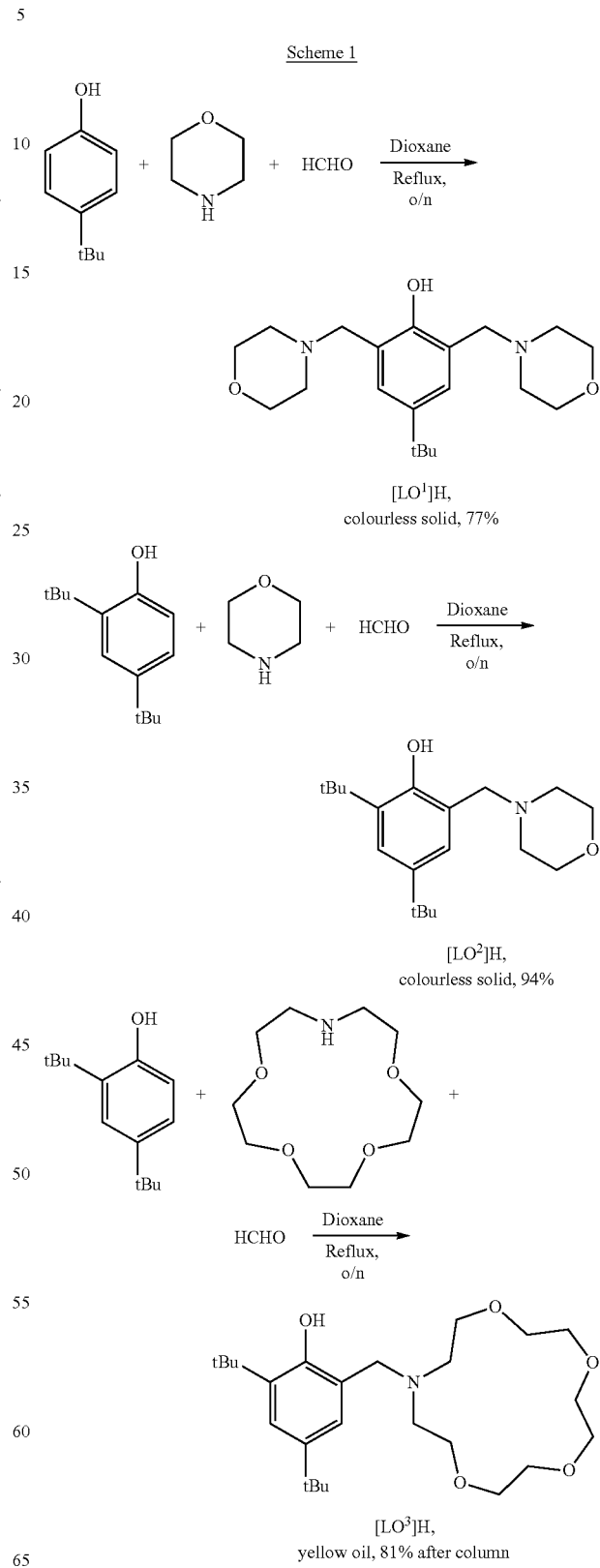

Scheme 1

Pro-ligand 2,6-bis(morpholinomethyl)-4-$^t$butyl-phenol ([LO$^1$]H)

11.7 mL of formaldehyde (solution 37 wt-% in water, 138.3 mmol) were added to 60 mL of a dioxane solution of 9.0 g of 4-$^t$butyl-phenol (60.6 mmol) and 10.3 mL of morpholine (10.2 g, 118.2 mmol). The mixture was refluxed overnight at a temperature of 120° C. The volatile fraction was removed in vacuum, and the resulting solid was extracted with toluene/water. The toluene layers were combined and dried over magnesium sulphate. After filtration, the yellow solution was concentrated under vacuum and stored overnight at a temperature of −24° C. Large, colourless crystals of [LO$^1$]H were obtained with a yield of 77%. The spectroscopic data for this compound ($^1$H and $^{13}$C{$^1$H}NMR) matched those already reported in literature, and its purity was further confirmed by elemental analysis. [LO$^1$]H is fully soluble in ethers, chlorinated solvents and aromatic hydrocarbon, and sparingly soluble in aliphatic hydrocarbons.

Pro-ligand 2,4-di-$^t$butyl-6-(morpholinomethyl)-phenol ([LO$^2$]H)

A yellow solution of 12.2 g of 2,4-di-$^t$butyl-phenol (59.1 mmol), 5.9 mL of formaldehyde (37 wt-% in water, 67.5 mmol) and 6.2 mL of morpholine (6.2 g, 70.9 mmol) was refluxed overnight in 90 mL of dioxane at a temperature of 120° C. The volatiles were pumped off, and the resulting sticky solid was extracted with toluene and a saturated aqueous solution of NaCl. The organic layers were combined, dried over MgSO$_4$, and the toluene was pumped off to yield an off-white solid, which was dried under vacuum to constant weight of 17.0 g with a yield of 94%. Single-crystals of [LO$^2$]H suitable for X-ray diffraction were grown from a concentrated pentane solution maintained overnight at a temperature of +4° C., and its structure was determined: it is represented in FIG. 1.

Elem. Anal. for C$_{19}$H$_{31}$NO$_2$ (305.46 g/mol): theoretical, C, 74.71, H, 10.23, N, 4.59%. found, C, 75.18, 10.23, N, 5.12%.

$^1$H NMR (CDCl$_3$, 200.13 MHz, 25° C.): δ 10.7 (br s, 1H, ArO—H), 7.26 (d, 1H, $^4J_{HH}$=1.7 Hz, arom. H), 6.88 (d, 1H, $^4J_{HH}$=1.7 Hz, arom. H), 3.79 (m, 4H, O—CH$_2$), 3.72 (s, 2H, Ar—CH$_2$—N), 2.60 (br s, 4H, N—CH$_2$—CH$_2$), 1.45 (s, 9H, C(CH$_3$)$_3$), 1.32 (s, 9H, C(CH$_3$)$_3$) ppm.

$^{13}$C{$^1$H} NMR (CDCl$_3$, 50.33 MHz, 25° C.): δ 153.9, 140.7, 123.6, 123.1, 120.0 (aromatic), 66.8 (O—CH$_2$), 62.6 (Ar—CH$_2$—N), 52.7 (N—CH$_2$—CH$_2$), 34.8 (C(CH$_3$)$_3$), 34.1 (C(CH$_3$)$_3$), 31.6 (C(CH$_3$)$_3$), 29.5 (C(CH$_3$)$_3$) ppm.

[LO$^2$]H is fully soluble in all common organic solvents, including aliphatic hydrocarbons.

Pro-ligand 2,4-di-$^t$butyl-6-[(1-aza-15-crown-5)methyl]-phenol ([LO$^3$]H)

A mixture of 1.03 g of 2,4-di-$^t$butyl-phenol (5.0 mmol), 0.5 mL of formaldehyde (37 wt-% in water, 6.2 mmol) and 1.25 g of 1-aza-15-crown-5 (5.7 mmol) was refluxed in 20 mL of dioxane for 24 h at a temperature of 120° C. The solvent was removed under vacuum to yield an orange oil which was dried to constant weight of 2.23 g with a crude yield. Purification by thin layer chromatography using pure chloroform as mobile phase allowed complete purification of the desired product, and 1.78 g of compound were obtained with a yield of 81% after evaporation of chloroform. Spectroscopic data for [LO$^3$]H matched rigorously those already given in the literature. [LO$^3$]H is a yellow viscous oil and is fully soluble in all organic solvents.

Synthesis of Divalent Metals Heteroleptic Complexes.

The synthesis of complexes based on zinc, magnesium and calcium is represented in scheme 2 herebelow.

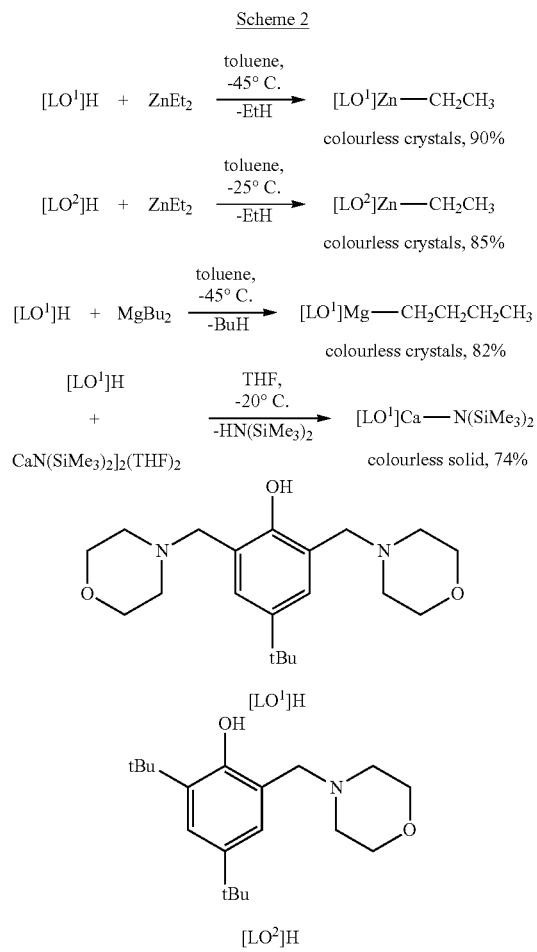

Synthesis of [2,6-bis(morpholinomethyl)-4-$^t$Bu-phenoxy]zinc-ethyl [[LO$^1$]ZnEt]

A solution of 3.5 g of [LO1]-H (10.0 mmol) in 75 mL of toluene was added at a temperature of −45° C. over a period of 20 minutes to a solution of 10.2 mL of ZnEt$_2$ (1.0 M solution in hexanes, 10.2 mmol) in 125 mL of in toluene. The resulting mixture was stirred at a temperature of −45° C. for a period of time of 60 min, and then at room temperature for a further 2 hours to give a white suspension. The precipitate was isolated by filtration and dried in vacuum to give analytically pure [LO$^1$]ZnEt as 4 g of a white powder with a yield of 91%. Colourless single-crystals of {[LO$^1$]ZnEt}$_2$·C$_6$H$_6$ were grown at room temperature from a concentrated benzene solution, and its solid-state structure was determined by X-ray crystallography.

Elem. Anal. for C$_{22}$H$_{36}$N$_2$O$_3$Zn (440.20 g/mol): theoretical, C, 59.79, H, 8.21, N, 6.34%. found C, 59.78, H, 8.21, N, 6.05%.

$^1$H NMR (CD$_2$Cl$_2$, 300.08 MHz, 25° C.): δ 7.15 (s, 2H, arom. H), 4.0-3.6 (br m, 12H, O—CH$_2$+Ar—CH$_2$—N), 2.7-2.3 (br m, 8H, N—CH$_2$—CH$_2$), 1.32 (s, 9H, C(CH$_3$)$_3$), 0.93 (t, 3H, $^3J_{HH}$=7.5 Hz, Zn—CH$_2$—CH$_3$), −0.02 (q, 2H, $^3J_{HH}$=7.5 Hz, Zn—CH$_2$—CH$_3$) ppm.

$^{13}C\{^1H\}$ NMR ($C_6D_6$, 50.33 MHz, 25° C.): δ 159.0, 140.4, 125.6 (aromatic), 66.2-66.0 (O—$CH_2$ and Ar—$CH_2$—N), 54.8 (N—$CH_2$—$CH_2$), 34.0 ($C(CH_3)_3$), 31.9 ($C(CH_3)_3$), 12.8 (Zn—$CH_2$—$CH_3$), 2.4 (Zn—$CH_2$—$CH_3$) ppm.

Figure 2:
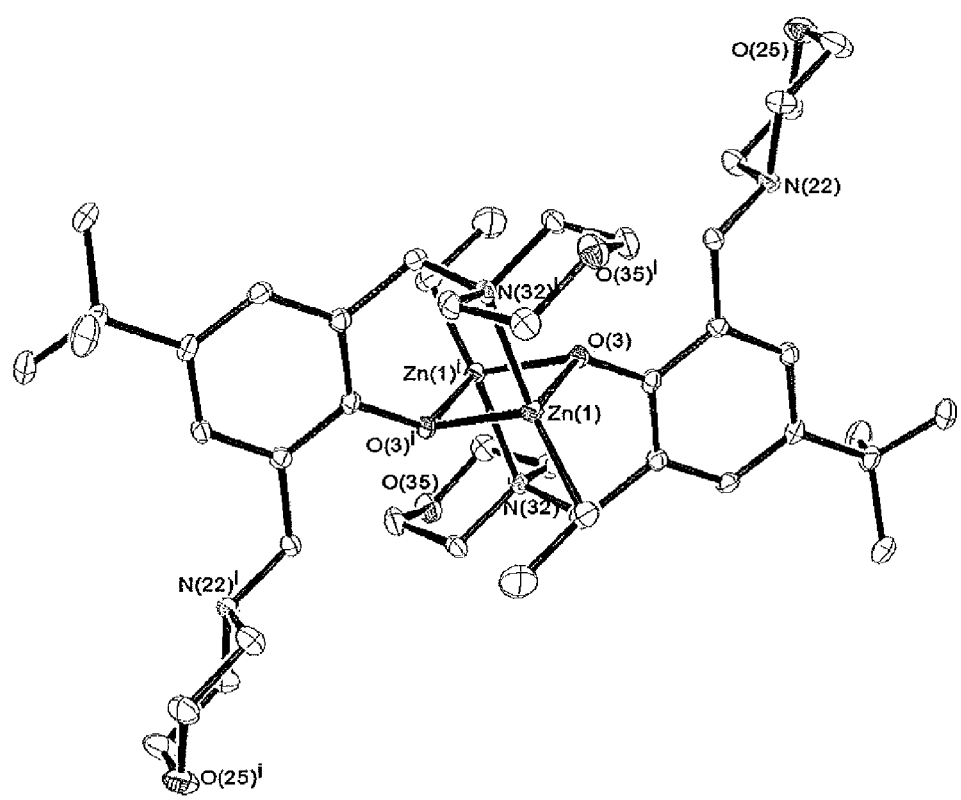
FIG. 2 represents the X-ray structure of complex [LO$^1$]ZnEt, wherein hydrogen atoms and benzene molecules are omitted for clarity.

Although the $^1H$ NMR spectra of [$LO^1$]ZnEt in $CD_2Cl_2$ or $C_6D_6$ seemingly appeared complicated, a full assignment of its $^1H$ and $^{13}C\{^1H\}$ NMR signals could be realised after 1-D ($^1H$, $^{13}C\{^1H\}$) and 2-D (COSY, HMBC and HMQC). NMR experiments were performed in toluene-d8 at −60° C. Its structure in the solid state was elucidated using X-ray quality crystals grown from a concentrated benzene solution stored at room temperature. It indicated that [$LO^1$]ZnEt exists as a dimeric species where the two zinc atoms are bridged by the oxygen atoms of the phenoxy moieties as seen in FIG. 2. [$LO^1$]ZnEt is soluble in ethers and dichloromethane, moderately soluble in benzene and toluene and insoluble in aliphatic hydrocarbons.

Synthesis of [2,4-di-$^t$butyl-6-(morpholinomethyl)-phenoxy]zinc-ethyl ([$LO^2$]ZnEt)

A solution of 1.06 g of [$LO^2$]H 3.47 mmol) in 20 mL of toluene was slowly added to a solution of 3.50 mL of $ZnEt_2$ (1.0 M solution in hexanes, 3.50 mmol) in 40 mL of toluene at a temperature of −25° C. and over a period of time of 20 minutes. The resulting product was obtained via alkane elimination as a colourless solution which was stirred at a temperature of −25° C. for a further 40 minutes. Evaporation of the solvent gave a white solid which was washed 3 times with 20 mL of pentane and dried under vacuum. It gave 1.18 g of complex with a yield of 85%.

Elem. Anal. for $C_{21}H_{35}NO_2Zn$ (397.20 g/mol): theoretical, C, 63.23, H, 8.84, N, 3.51%. found C, 63.09, H, 8.73, N, 3.51%.

$^1H$ NMR ($C_6D_6$, 500.13 MHz, 25° C.): δ 7.58 (d, 1H, $^4J_{HH}$=2.6 Hz, arom. H), 6.88 (d, 1H, $^4J_{HH}$=2.6 Hz, arom. H), 3.6-3.3 (br m, 6H, O—$CH_2$+Ar—$CH_2$—N), 3.30 (br s, 2H, N—$CH_2$—$CH_2$), 2.60 (br, 2H, N—$CH_2$—$CH_2$), 1.66 (s, 9H, $C(CH_3)_3$), 1.39 (m, 3H, Zn—$CH_2$—$CH_3$), 1.37 (s, 9H, $C(CH_3)_3$), 0.54 (br s, 2H, Zn—$CH_2$—$CH_3$) ppm.

$^{13}C\{^1H\}$ NMR ($C_6D_6$, 125.76 MHz, 25° C.): δ 159.7, 139.5, 139.0, 129.3, 125.5, 123.9 (aromatic), 65.0 (O—$CH_2$), 64.8 (Ar—$CH_2$—N), 54.7 (N—$CH_2$—$CH_2$), 35.7 (C($CH_3$)$_3$), 34.1 ($C(CH_3)_3$), 31.9 ($C(CH_3)_3$), 31.3 ($C(CH_3)_3$), 12.9 (Zn—$CH_2$—$CH_3$), 3.4 (Zn—$CH_2$—$CH_3$) ppm. The complex is soluble in THF and diethyl ether, but has a limited solubility in toluene and is not soluble in light petroleum ether.

Synthesis of [2,4-di-$^t$butyl-6-(morpholinomethyl)-phenoxy]magnesium-butyl ([$LO^1$]MgBu)

In a procedure identical to that described for [$LO^2$]ZnEt, compound [$LO^1$]MgBu was obtained with a yield of 82% by reaction of 0.94 g of [$LO^1$]H (2.70 mmol) with 3.0 mL of $MgBu_2$ (1.0 M solution in heptanes, 3.50 mmol) in 22.0 mL of toluene.

Elem. Anal. for $C_{24}H_{40}N_2O_3Mg$ (428.90 g/mol): theoretical, C, 67.21, H, 9.40, N, 5.67%. found C, 67.32, H, 9.89, N, 6.19%.

$^1H$ NMR ($C_6D_6$, 500.13 MHz, 25° C.): δ 7.27 (br s, 2H, arom. H), 4.1-3.1 (br m, 12H, O—$CH_2$+Ar—$CH_2$—N), 2.45 (br s, 8H, N—$CH_2$—$CH_2$), 41.68 (m, 2H, $^3J_{HH}$=7.5 Hz, Mg—$CH_2$—$CH_2$—$CH_2$—$CH_3$), 1.39 (m, 2H, $^3J_{HH}$=7.5 Hz, Mg—$CH_2$—$CH_2$—$CH_2$—$CH_3$), 1.38 (s, 9H, C($CH_3$)$_3$), 1.03 (t, 3H, $^3J_{HH}$=7.5 Hz, Mg—$CH_2$—$CH_2$—$CH_2$—$CH_3$), −0.15 (t, 2H, $^3J_{HH}$=7.5 Hz, Mg—$CH_2$—$CH_2$—$CH_2$—$CH_3$) ppm.

$^{13}C\{^1H\}$ NMR ($C_6D_6$, 125.76 MHz, 25° C.): δ 156.3, 140.9, 128.3 (aromatic), 66.2 (O—$CH_2$), 61.2 (Ar—$CH_2$—N), 54.5 (N—$CH_2$—$CH_2$), 34.0 ($C(CH_3)_3$), 32.6 (Mg—$CH_2$—$CH_2$—$CH_2$—$CH_3$), 31.9 (Mg—$CH_2$—$CH_2CH_2$—$CH_3$), 31.8 ($C(CH_3)_3$), 14.6 (Mg—$CH_2$—$CH_2$—$CH_2$—$CH_3$), 9.4 (Mg—$CH_2$—$CH_2$—$CH_2$—$CH_3$).

The complex is soluble in THF and diethyl ether, but has a limited solubility in toluene and is not soluble in light petroleum ether.

Synthesis of [2,6-bis(morpholinomethyl)-4-$^t$Bu-phenoxy]calcium-[bis(trimethylsilyl)amide] [[$LO^1$]CaN(SiMe$_3$)$_2$]

A solution of 1.32 g of [$LO^1$]H (3.79 mmol) in 20 mL of THF was added at room temperature over a period of time of 45 minutes to 20 mL of a THF solution of 1.71 g of Ca[N(SiMe$_3$)$_2$]$_2$(THF)$_2$ (3.39 mmol). The yellow solution was stirred overnight at room temperature, and the solvent was evaporated under vacuum to give a white powder. Repeated extraction with hot hexanes (heptane or higher hydrocarbons can also be used) followed by evaporation of the solvent and drying in vacuo afforded the analytically pure heteroleptic compound with a yield of 77%. Single crystals of [$LO^1$]CaN(SiMe$_3$)$_2$ were grown by slow diffusion of hexane in a THF solution at room temperature, and its solid-state structure was elucidated by X-ray diffraction.

Elem. Anal. for $C_{26}H_{49}N_3O_3Si_2Ca$ (547.29 g/mol): theoretical, C, 56.99, H, 9.01, N, 7.67%. found C, 56.88, H, 8.95, N, 7.51%.

$^1H$ NMR ($C_6D_6$, 200.13 MHz, 25° C.): δ 7.17 (br s, 2H, arom. 3.69 (br, 12H, O—$CH_2$+Ar—$CH_2$—N), 2.62 (br s, 8H, N—$CH_2$—$CH_2$), 1.34 (s, 9H, C($CH_3$)$_3$), −0.01 (s, 18H, Si($CH_3$)$_3$) ppm.

$^{13}C\{^1H\}$ NMR ($C_6D_6$, 50.33 MHz, 25° C.): δ 159.0, 139.5, 129.9, 124.2 (aromatic), 64.6 (O—$CH_2$), 60.5 (Ar—$CH_2$—N), 54.1 (N—$CH_2$—$CH_2$), 33.8 ($C(CH_3)_3$), 31.8 ($C(CH_3)_3$), 5.8 (Si($CH_3$)$_3$) ppm.

Figure 3:
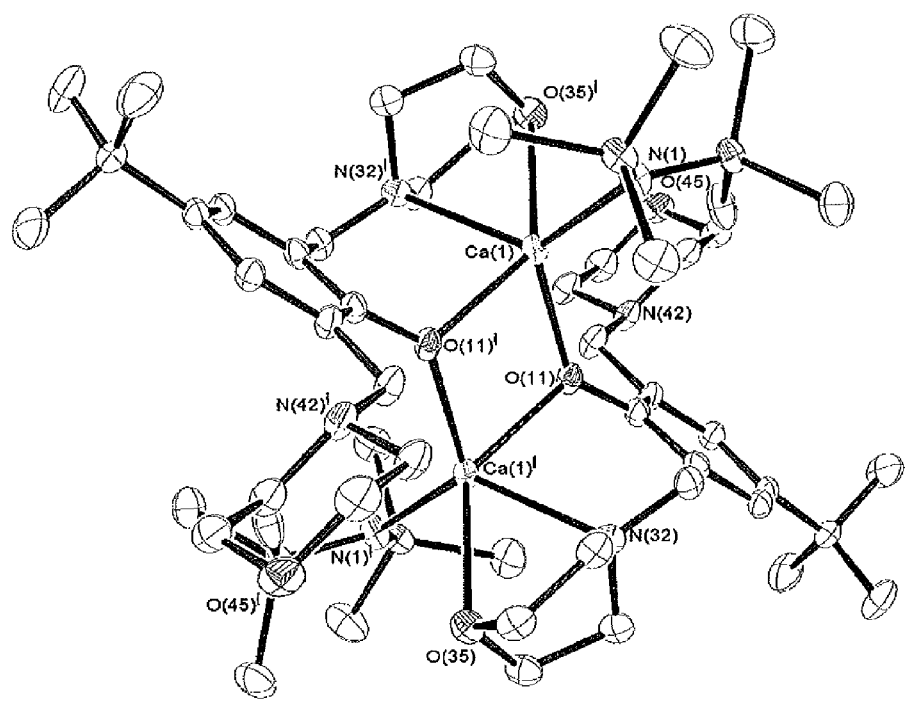
FIG. 3 represents the X-ray structure of dimer [LO$^1$]CaN(SiMe$_3$)$_2$ wherein hydrogen atoms are omitted for clarity.

The solid-state structure of [$LO^1$]CaN(SiMe$_3$)$_2$ is represented in FIG. 3: it indicates that the compound exists under the form of a dimeric species bridged by the oxygen atoms of the phenoxy moieties.

The solubility of [$LO^1$]CaN(SiMe$_3$)$_2$ in usual organic solvents is good to excellent, even in aliphatic hydrocarbons. Its stability in solution is very good, as no sign of decomposition can be seen after storage of a $C_6D_6$ solution in an NMR tube for 5 days; moreover, its heteroleptic nature is preserved in solution as indicated by the absence of a Schlenk-type equilibrium involving only [$LO^1$]CaN(SiMe$_3$)$_2$ even after prolonged reaction time in $C_6D_6$ at 80° C. There is no sign of formation of Ca[N(SiMe$_3$)$_2$]$_2$ and [$LO^1$]$_2$Ca.

It is an essential advantage of the present invention that, starting from commercial sources, the complete syntheses of ligands [$LO^1$]H and [$LO^2$]H, and the further syntheses of complexes [$LO^1$]ZnEt, [$LO^2$]ZnEt and [$LO^1$]MgBu can be achieved in at most 48 h to give analytically pure compounds on a multi-gram scale. By comparison, the synthesis of zinc-based initiator (BDI)ZnN(SiMe$_3$)$_2$ used for the efficient ROP of LA, BBL or TMC requires two full weeks and harsh conditions.

Synthesis of Chain Transfer Agent.

Synthesis of 1-(Benzyloxy)-2-phenyl-2-(2',2',6',6'-tetramethyl-1'-piperidinyloxy)-ethane (AA-OH)

The synthesis of AA-OH is schematically represented in scheme 3.

Scheme 3

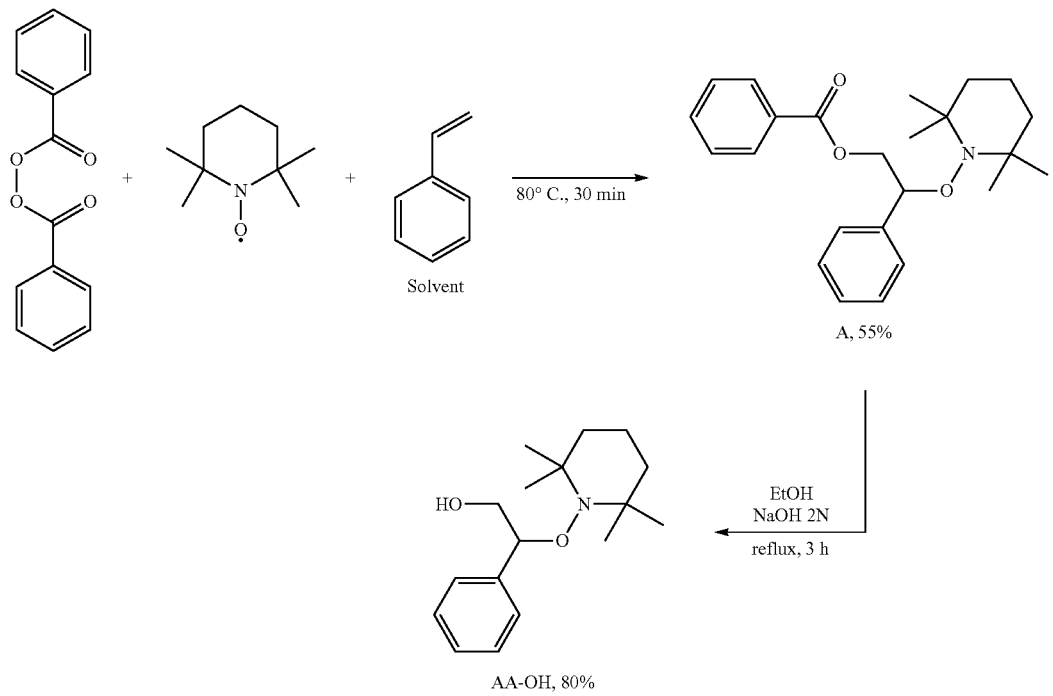

It was carried out by modifying the existing procedure described in Hawker et al. (C. J. Hawker, G. G. Barclay, A. Oreliana, J. Dao, W. Devonport, *Macromolecules*, 1996, 29, 5245-5254) or in Asri et al. (M. Asri Abd Ghani, D. Abdallah, P. M. Kazmaier, B. Keoshkerian, E. Buncel, *Can. J. Chem.*, 2004, 82, 1403-1412). To a solution of TEMPO in distillated styrene, 1.14 equivalents of benzoyl peroxide (75% in water) were slowly added. Upon heating to a temperature of 80° C. for a period of time of 30 minutes, the reaction mixture turned successively red, yellow and finally green. The volatiles were removed under vacuum, and a white powder precipitated from the resulting green oily material on addition of pentane. After removal of the powder by filtration, the solvent was evaporated, yielding a green oil that was then dissolved in methanol. Re-crystallisation at a temperature of –4° C. gave the pure benzylated product A with a yield of 55%.

A mixture of compound 3.1 g of A and 15 mL of a 2N NaOH aqueous solution was then refluxed in ethanol for a period of time of 3 h. Evaporation of the volatile fraction afforded an oily material. After extraction with dichloromethane/water, the combined organic layers were dried over $MgSO_4$, and the solvent was removed in vacuum to give an orange oil which was dried to constant weight with a yield of 80%; characterisation of this material by NMR spectroscopy ($^1H$, $^{13}C\{^1H\}$, and COSY experiments) and elemental analysis confirmed the expected composition and purity of AA-OH.

Polymerisation of Cyclic Esters and Cyclic Carbonates.

Polymerisation of Lactide in Toluene or THF.

The general polymerisation procedure is represented in scheme 4.

Scheme 4

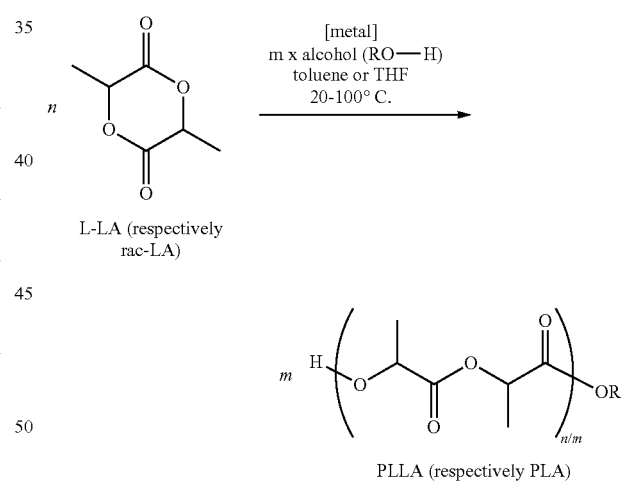

1. $[LO^1]ZnEt$.

The immortal ROP of LA with new initiator $[LO^1]ZnEt$ in presence of an alcohol transfer agent is extremely rapid and well-controlled, and provides a catalytic system for the ROP with no equivalent in the literature. The polymerisation conditions and results are summarised in Table I.

TABLE I

| Ex | Solvent | Alcohol | LA/Zn/ROH | [LA] mol/L | T (°C.) | t (min) | Yield (%) | $\overline{Mn}_{theo}$ (g/mol) | $\overline{Mn}_{GPC}$ (g/mol) | PDI | $P_m$ |
|---|---|---|---|---|---|---|---|---|---|---|---|
| 0 | toluene | iPrOH | L 1000/—/10 | 2 | 60 | 60 | 0 | — | — | — | — |
| 1 | toluene | — | L 1000/1/0 | 2 | 80 | 60 | 91 | 130 000 | 65 000 | 1.50 | nd |
| 1bis | toluene | — | L 1000/1/0 | 2 | 60 | 60 | 18 | 26 000 | 10 300 | 2.24 | nd |
| 2 | toluene | iPrOH | L 500/1/10 | 2 | 60 | 60 | 98 | 7 100 | 7 500 | 1.10 | nd |
| 3 | toluene | iPrOH | L 1000/1/10 | 2 | 60 | 15 | 20 | 2 900 | 4 700 | 1.09 | nd |
| 4 | toluene | iPrOH | L 1000/1/10 | 2 | 60 | 60 | 97 | 14 000 | 15 100 | 1.10 | 1.00 |
| 5 | toluene | AA-OH | L 1000/1/10 | 2 | 60 | 60 | 95 | 14 000 | 13 000 | 1.10 | nd |
| 6 | toluene | iPrOH | Rac 1000/1/10 | 2 | 60 | 60 | 99 | 14 300 | 12 200 | 1.20 | 0.50 |
| 7 | THF | iPrOH | L 1000/1/10 | 2 | 60 | 60 | 57 | 8 400 | 9 200 | 1.08 | nd |
| 8 | THF | iPrOH | Rac 1000/1/10 | 2 | 60 | 60 | 68 | 13 000 | 12 700 | 1.19 | 0.45 |
| 9 | toluene | iPrOH | L 5000/1/25 | 4 | 60 | 90 | 94 | 27 100 | 26 200 | 1.16 | nd |
| 10 | — | iPrOH | L 5000/1/25 | Bulk | 115 | 90 | 63 | 18 200 | 18 000 | 1.18 | nd |
| 11 | toluene | iPrOH | L 10000/1/50 | 6 | 60 | 4 × 60 | 98 | 28 200 | 26 700 | 1.22 | nd |
| 11bis | toluene | iPrOH | L 20000/1/50 | 6 | 60 | 3 × 60 | 89 | 51 300 | 36 400 | 1.37 | n.d. |
| 12 | toluene | iPrOH | L 20000/1/100 | 6 | 60 | 4 × 60 | 95 | 27 400 | 26 300 | 1.28 | nd |
| 12bis | toluene | iPrOH | L 20000/1/175 | 6 | 60 | 3 × 60 | 98 | 16 200 | 16 100 | 1.20 | nd |
| 13 | toluene | iPrOH | L 20000/1/250 | 6 | 60 | 3 × 60 | 98 | 11 300 | 11 600 | 1.26 | nd |
| 13bis | toluene | iPrOH | L 20000/1/500 | 6 | 60 | 3 × 60 | 97 | 5 600 | 5 400 | 1.32 | nd |
| 13ter | toluene | iPrOH | L 20000/1/750 | 6 | 60 | 3 × 60 | 94 | 3 600 | 3 000 | 1.46 | nd |
| 13tet | toluene | iPrOH | L 20000/1/1 000 | 6 | 60 | 3 × 60 | 99 | 2 900 | 2 400 | 1.33 | nd |
| 14 | toluene | iPrOH | L 50000/1/250 | 6 | 60 | 8 × 60 | 86 | 24 800 | 17 700 | 1.43 | nd |
| 15 | toluene | iPrOH | L 50000/1/500 | 6 | 60 | 16 × 60 | 100 | 14 500 | 13 500 | 1.60 | nd |

In this table, the yield is measured after precipitation in methanol, the theoretical number average molecular weight $M_n$ is calculated using formula $[LA]_0[POH]_0 \times$ monomer conversion $\times ML_A + M_{iPrOH}$ wherein $ML_A = 144$ g/mol and $M_{iPrOH} = 60$ g/mol. $M_{nGPC}$ is determined by gel permeation chromatography vs. polystyrene standards and corrected by a mark-Houwink factor of 0.58. $P_m$ is the probability of meso linkage of lactide units and is determined by examination of the methine region in the homodecoupled $^1$H NMR spectrum of the polymers recorded at room temperature in $CDCl_3$.

Polymerisation of 1 000 equiv. of L-LA in toluene with [LO$^1$]ZnEt in the absence of alcohol (example 1 of Table I) is rapid at 80° C. (91% conversion in 60 min), but poorly controlled, as indicated by a rather broad polydispersity index (PDI) of 1.50 and poor correlation between expected and observed number average molecular weights Mn. However, it is much slower and very poorly controlled at 60° C. (example 1bis). Upon addition of 10 equivalents of iPrOH (example 4), the ROP is faster than without alcohol and very well controlled as indicated by a PDI of 1.10, and by the excellent agreement between theoretical and experimental number average molecular weights $M_n$. Besides, under these conditions, the catalytic system operates the complete polymerisation of the optically active monomer without any epimerisation, as indicated by examination of the methine region in the homodecoupled $^1$H NMR spectrum of PLLA$_4$ with $P_m = 1.00$ wherein index 4 after PLLA refers to the example number.

Comparison of examples 3 and 4 indicates that the initial stage of the polymerisation with system [LO$^1$]ZnEt/iPrOH wherein the ratio Zn/alcohol is of 1:10 is slow, as only 20% conversion was reached after a period of time of 20 min as seen in example 3 as compared to example 4 showing quantitative conversion after a period of time of 60 min, all other conditions being the same. This suggests the presence of an induction period for this catalyst.

An overview of Table 1 indicates that an extremely large number of equiv. of L-LA can be polymerised in a controlled fashion with [LO$^1$]ZnEt in presence of alcohol. Both the polydispersity indexes and the correlation between expected and observed molecular weights remain good to excellent when monomer loading is increased, even for L-LA/[LO$^1$] ZnEt ratios of up to 50 000. Conversions are quantitative, under the conditions employed, for ratios L-LA/[LO$^1$]ZnEt ranging between 500 and 50 000. Besides, it is remarkable that a very large excess of transfer agent, typically iPrOH, can be used, in a range between 1 and 1 000 equivalents of iPrOH per metal centre, with no visible detrimental effect on the control of the polymerisation parameters. The present catalytic system combines remarkable productivity and degree of control.

Concentrations of monomer in toluene of up to 6.0 M can be used, as the rapid conversion of the monomer facilitates its complete dissolution in the aromatic solvent. At high conversion, all of the monomer dissolves in the reaction medium, whereas the resulting polymer is not soluble and precipitates at high conversion. The evolution of the reaction can therefore be readily monitored in a visual manner.

The ROP of LA in coordinating solvents such as THF is slower than in non-coordinating solvents such as toluene, as can be seen by comparing examples 4 (toluene; 97% conv.) and 7 (THF, 57% conv.); this decrease in polymerisation kinetics results from the fact that in coordinating solvents, coordination onto the metal centre by the monomer is impeded by that of the solvent. Nevertheless, the polymerisation in THF remains very well controlled.

The polymerisation of the racemic mixture of isomers (rac-LA) by [LO$^1$]ZnEt/iPrOH with a ratio Zn/alcohol of 1:10 is not stereo-selective as indicated in example 6 (toluene, $P_m$=0.50) and in example 8 (THF, $P_m$=0.45).

Figure 4:
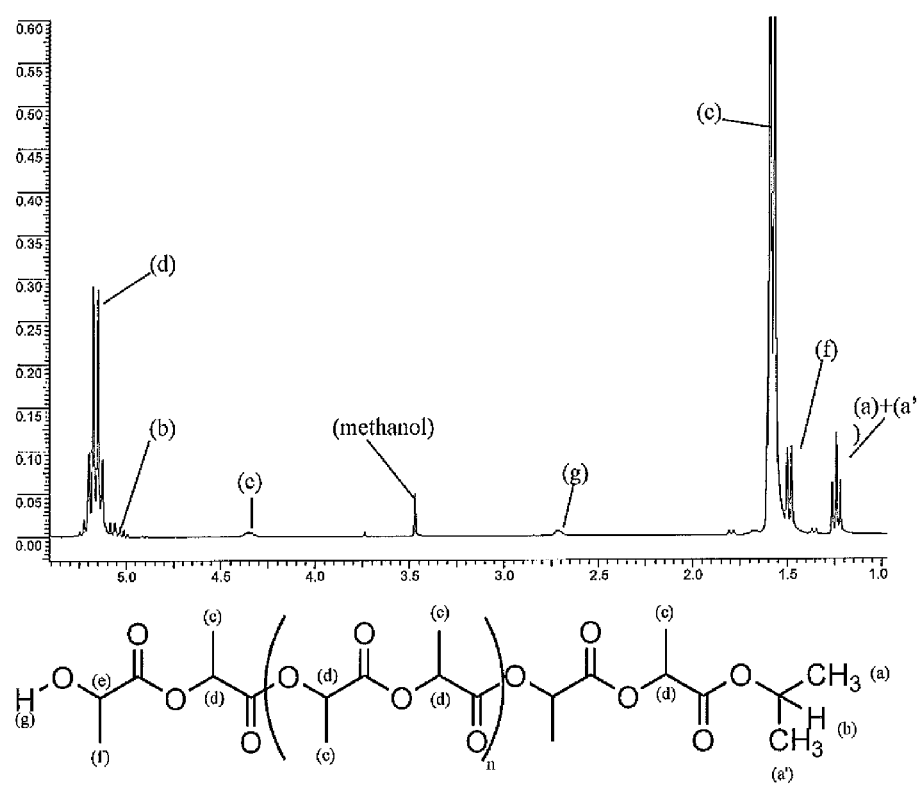
FIG. 4 represents the $^1$H NMR (500.13 MHz, CDCl$_3$, 25° C., 16 scans, D1=0.50 sec) spectrum of a low molecular weight PLLA prepared with L-LA/[LO$^1$]ZnEt/iPrOH in relative amounts of 100/1/10.
Figure 5A:
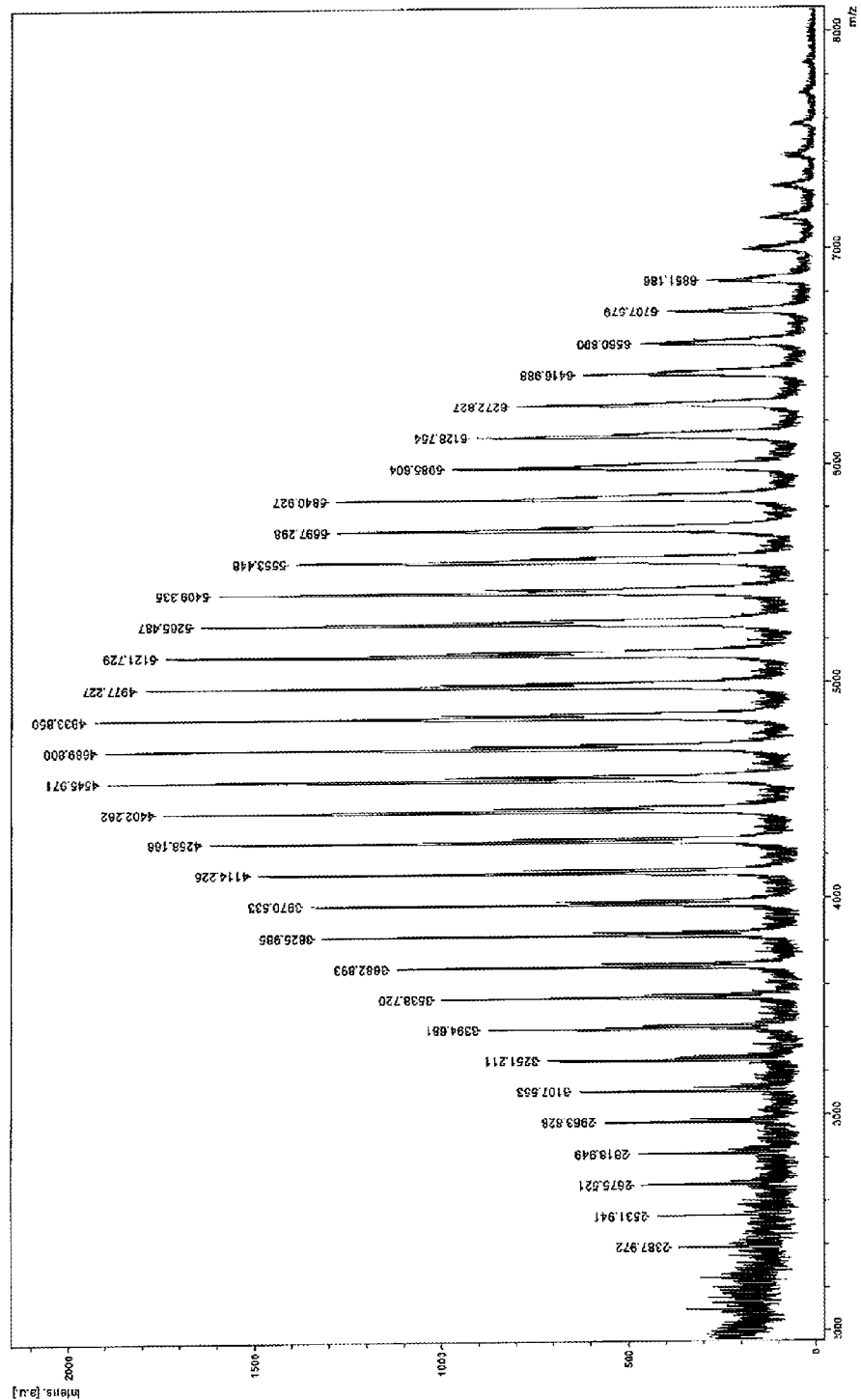
FIGS. 5A and 5B represent the high resolution MALDI-TOF mass spectrum (main population: Na$^+$; minor population: K$^+$) of a low molecular weight PLLA having a number average molecular weight $\overline{Mn}_{GPC}$ of 4 700 g/mol, prepared with L-LA/[LO$^1$]ZnEt/iPrOH in relative amounts of 1 000/1/10 with a 20% conversion.
Figure 5B:
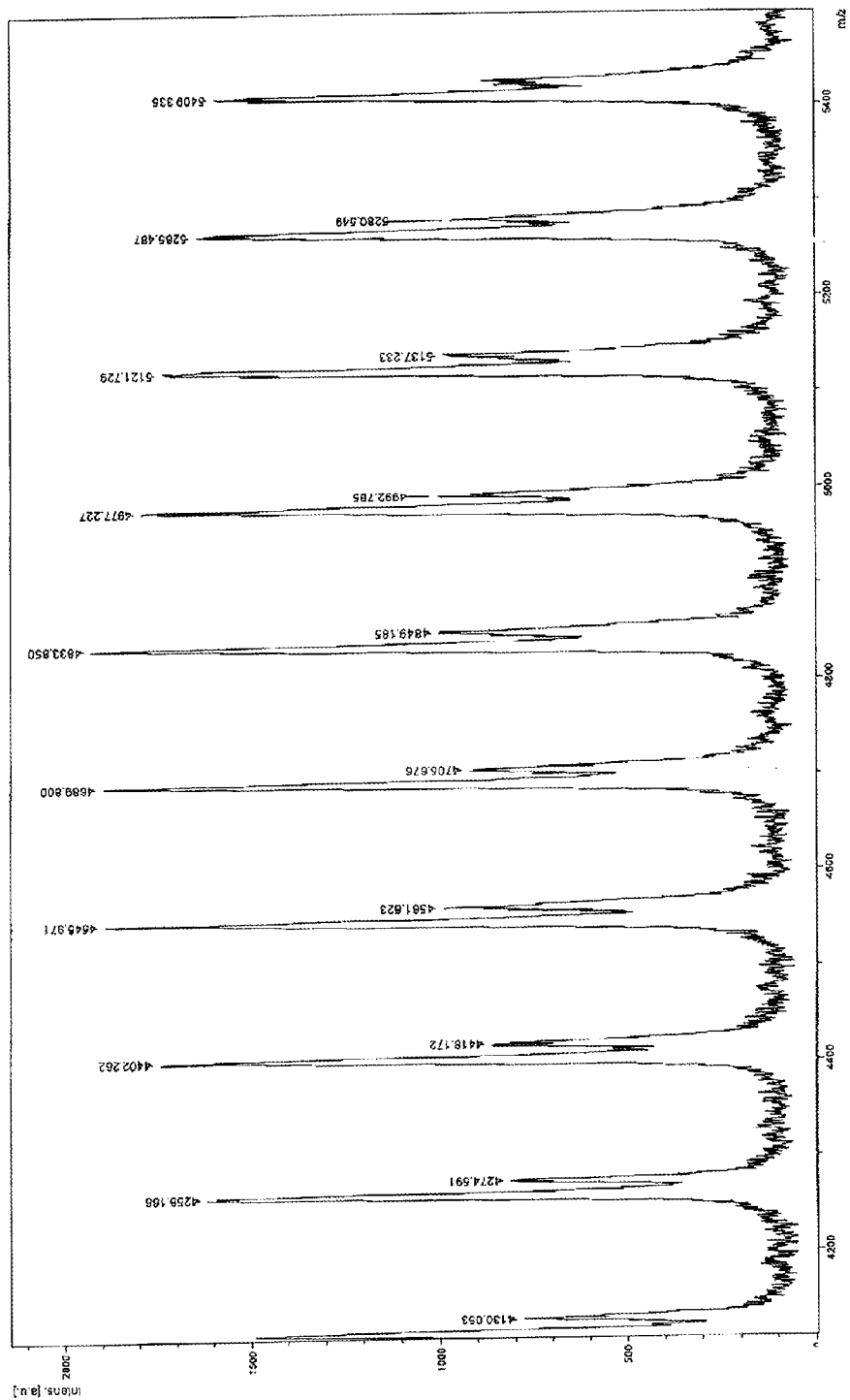
Figure 6A:
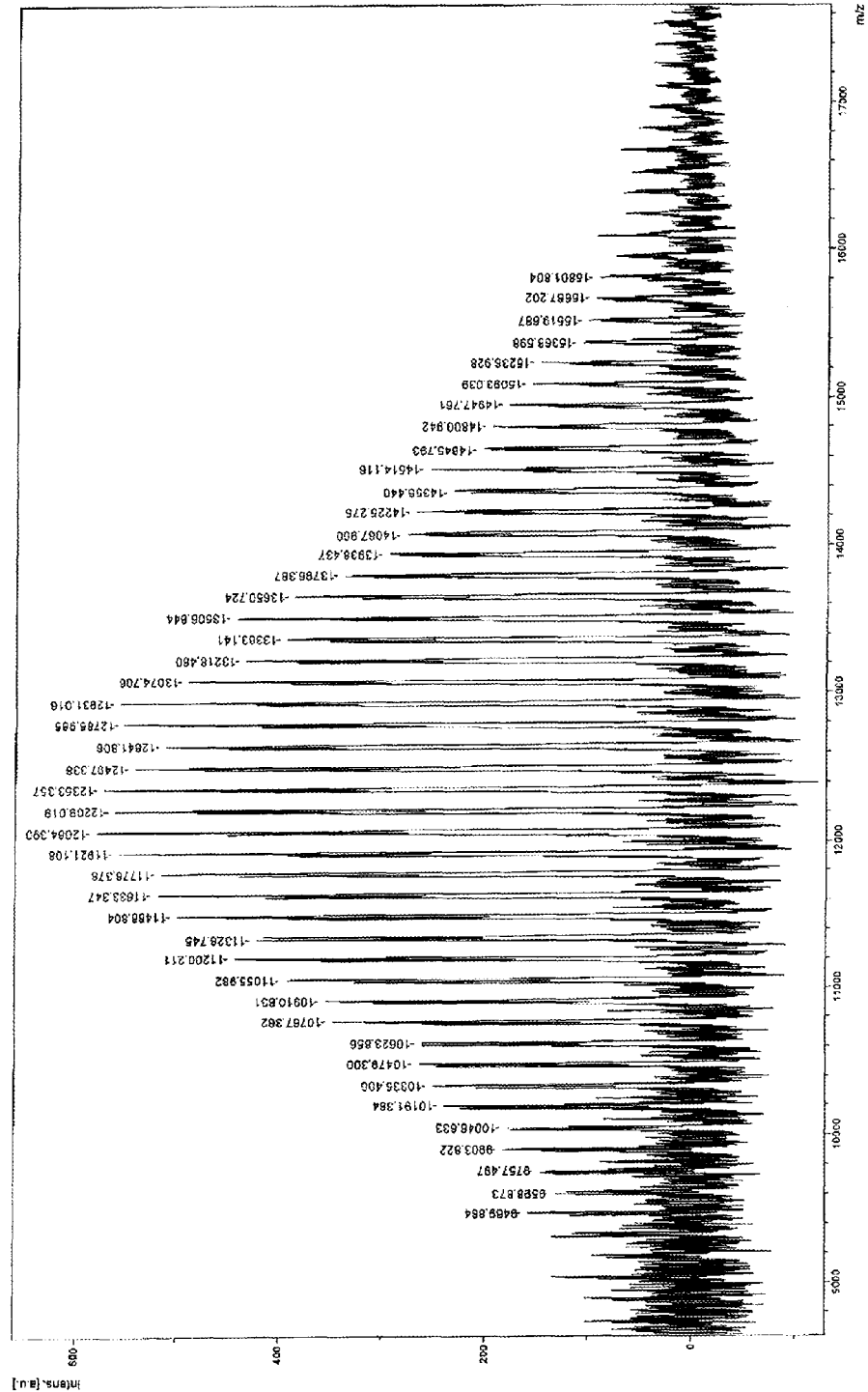
FIGS. 6A and 6B represent the MALDI-TOF mass spectrum (minor population: Na$^+$; main population: K$^+$) of a medium molecular weight PLLA having a number average molecular weight $\overline{Mn}_{GPC}$ of 13 200 g/mol, prepared with L-LA/[LO$^1$]ZnEt/iPrOH in relative amounts of 2 500/1/25 with a 98% conversion.
Figure 6B:
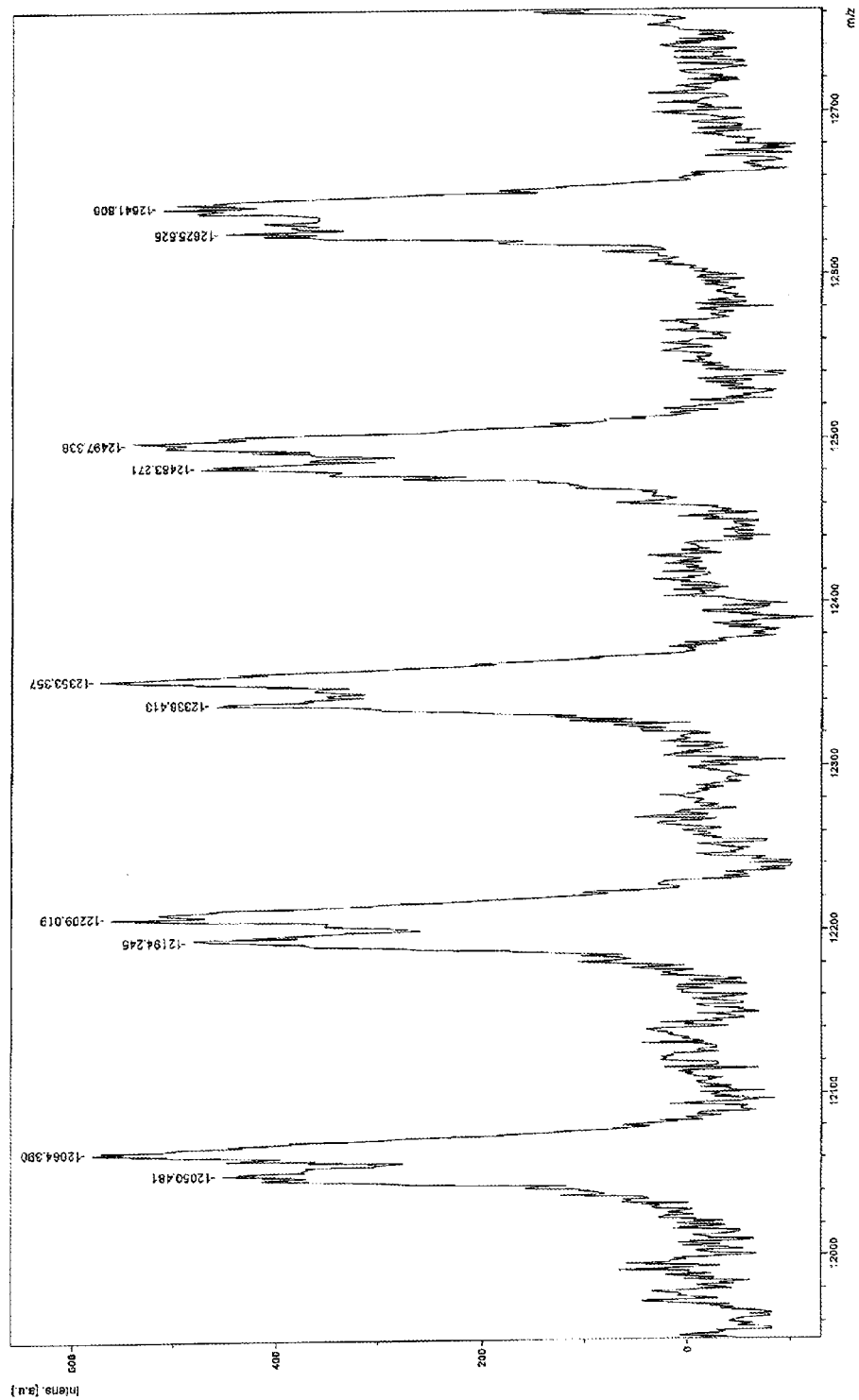

The nature of a single initiating group—namely, the isopropoxy group OCH(CH$_3$)$_2$— in the catalytic system [LO$^1$]ZnEt/iPrOH was demonstrated by the means of NMR spectroscopy and MALDI-TOF mass spectrometry. The $^1$H NMR spectrum of a low molecular weight PLLA prepared specifically with L-LA/[LO$^1$]ZnEt/iPrOH in relative amounts of 100/1/10 is represented in FIG. 4. The presence of —OCH(CH$_3$)$_2$ end-groups is evidenced by the diagnostic signals at δ 5.06 and 1.24 ppm; there is no indication of the presence of PLLA chains initiated by either Et- or [LO$^1$]- groups. This analysis was further corroborated by inspection of the MALDI-TOF mass spectra of two PLLAs prepared with [LO$^1$]ZnEt/iPrOH and having respectively a molecular weight of 4 700 g/mol, represented in FIGS. 5A-5B and a molecular weight of 13 200 g/mol, represented in FIGS. 6A-6B. In both spectra, there is a very good agreement between the theoretical molecular weights of isopropoxy-terminated PLLA chains and with the GPC experimental results. For each spectrum, two Gaussian distributions were observed, wherein the first and second populations correspond respectively to ionisation with Na$^+$ and K$^+$ [Δ(m/z)=16 Da between the two populations as can be seen in FIGS. 5(B) and 6(B)]. The molecular weight of each peak is consistent with the calculated molecular weights for the on-matrix compounds (H)(C$_6$H$_8$O$_4$)$_n$(OiPr)(Na) and (H)(C$_6$H$_8$O$_4$)$_n$(OiPr)(K), wherein n is the degree of polymerisation. On each spectrum, repeated increments of 144 Da between consecutive peaks in a same population are a definitive proof that undesirable trans-esterification reactions generally promoted by the zinc complex do not take place in the course of polymerisation to a significant extent, even at complete conversion of the monomer. Those polymers are therefore void of cyclic macromolecules.

As also evidenced in Table I, iPrOH proved an extremely efficient chain transfer agent for the immortal, controlled ROP of a large excess of LA with [LO$^1$]ZnEt. However, this methodology is not restricted to iPrOH, and other alcohols can be efficiently used in its place, such as for example benzyl alcohol, TEMPO-OH, HEMA or various hydroxy-alkoxyamines. This is successfully illustrated by examination of examples 4 and 5: kinetics and control of the polymerisation parameters are identical in both cases. Thus, iPrOH can be substituted adequately for example by AA-OH.

2. [LO$^2$]ZnEt.

The polymerisation conditions and results are summarised in Table II.

TABLE II

| Ex | Solvent | Alcohol | LA/Zn/ROH | [LA] (mol/L) | T (° C.) | t min | Yield (%) | $\overline{Mn}_{theo}$ (g/mol) | $\overline{Mn}_{GPC}$ (g/mol) | PDI | $P_m$ |
|---|---|---|---|---|---|---|---|---|---|---|---|
| 16 | toluene | iPrOH | L 1 000/1/10 | 2 | 60 | 15 | 0 | — | — | — | — |
| 17 | toluene | iPrOH | L 1 000/1/10 | 2 | 60 | 60 | 98 | 14 100 | 15 100 | 1.09 | 1.00 |
| 18 | toluene | iPrOH | Rac 1 000/1/10 | 2 | 60 | 60 | 100 | 14 500 | 12 000 | 1.20 | 0.45 |
| 19 | THF | iPrOH | Rac 1 000/1/10 | 2 | 60 | 60 | 92 | 13 300 | 9 100 | 1.32 | 0.40 |
| 20 | toluene | iPrOH | L 5 000/1/25 | 4 | 60 | 90 | 92 | 26 500 | 26 300 | 1.12 | nd |

The immortal ring-opening polymerisation of LA with initiator [LO$^2$]ZnEt in presence of an alcohol as transfer agent is extremely rapid and well-controlled. The polymerisation of 1 000 equiv. of L-LA in toluene with 10 equivalents of iPrOH is achieved within 60 min at a temperature of 60° C. as can be seen in example 17 of Table II. Nearly quantitative conversion of 5 000 equiv. of L-LA in toluene with 25 equivalents of iPrOH requires 90 min at a temperature of 60° C. High monomer or alcohol loadings bear little influence on the control of the polymerisation parameters: the polydispersity index is maintained around 1.10 and the agreement between theoretical and observed number average molecular weights Mn is nearly perfect. As mentioned for the ROP with complex [LO$^1$]ZnEt, comparison of examples 16 (reaction time=15 min, no conversion) and 17 (reaction time=60 min, quantitative conversion) also clearly reveals the existence of an activation period of at least 15 min, for the catalytic system [LO$^2$]ZnEt/iPrOH. The polymerization of 1 000 equivalents of rac-LA is very fast in toluene (complete conversion in example 18) as well as in THF (92% conversion in example 19). It is well controlled in both cases, although there is a slight discrepancy between expected and observed molecular weights and a somewhat broader distribution in the latter case. The catalytic system exhibits a slight propensity for the formation of syndiotactic PLA, which is more pronounced in THF with $P_m$=0.40 than in toluene with $P_m$=0.45.

3. [LO$^1$]MgBu.

The polymerisation conditions and results are summarised in Table III.

TABLE III

| Ex | Solvent | Alcohol | LA/Mg/ROH | [LA] mol/L | T (° C.) | t (min) | Yield (%) | $\overline{M}n_{theo}$ (g/mol) | $\overline{M}n_{GPC}$ (g/mol) | PDI | $P_m$ |
|----|---------|---------|-----------|------------|----------|---------|-----------|---------|---------|------|-------|
| 21 | toluene | iPrOH | L 1 000/1/10 | 2 | 60 | 15 | 95 | 13 700 | 15 300 | 1.14 | 1.00 |
| 22 | toluene | iPrOH | Rac 1 000/1/10 | 2 | 60 | 15 | 99 | 14 300 | 15 200 | 1.21 | 0.54 |
| 23 | THF | iPrOH | Rac 1 000/1/10 | 2 | 60 | 15 | 90 | 13 000 | 12 700 | 1.19 | 0.41 |
| 24 | toluene | iPrOH | L 5 000/1/25 | 4 | 60 | 90 | 79 | 22 700 | 20 500 | 1.14 | nd |
| 25 | toluene | iPrOH | L 5 000/1/50 | 4 | 60 | 90 | 71 | 10 200 | 9 400 | 1.15 | nd |
| 26 | toluene | iPrOH | L 5 000/1/100 | 4 | 60 | 90 | 71 | 5 200 | 5 200 | 1.12 | nd |
| 27 | toluene | iPrOH | L 5 000/1/50 | 4 | 80 | 120 | 88 | 12 700 | 13 200 | 1.13 | nd |
| 28 | toluene | iPrOH | L 10 000/1/25 | 6 | 80 | 8 × 60 | 52 | 30 000 | 22 400 | 1.28 | nd |
| 29 | toluene | iPrOH | L 10 000/1/50 | 6 | 80 | 8 × 60 | 53 | 15 300 | 14 100 | 1.15 | nd |

Magnesium complex [LO$^1$]MgBu constitutes a very efficient initiator for the ROP of LA, and, in association with alcohol, promotes the rapid and controlled immortal polymerisation of the cyclic di-ester. For instance, the polymerisation of 1 000 equivalents of L-LA with 10 equivalents of iPrOH as transfer agent was nearly quantitative as seen in example 21 of Table III; it was completed in 15 min, very well controlled and proceeded without noticeable epimerisation of the stereo-centres as indicated by a $P_m$ of 1.00.

High loadings of L-LA ranging between 1 000 to 5 000 equivalents per metal centre, with a large excess of transfer agent (here iPrOH), ranging between 10 and 100 equivalents with respect to Mg, were polymerised typically within 2 h at temperatures ranging between 60 and 80° C. In all cases, the polydispersity index was very narrow and ranged between 1.11 and 1.21, and the correlation between expected and experimental molecular weights were close to ideal.

Unlike its Zn-based analogues [LO$^1$]ZnEt and [LO$^2$]ZnEt, [LO$^1$]MgBu was fairly sensitive to both monomer purity and transfer agent loadings. At a temperature of 60° C., increasing the number of equivalents of iPrOH from 25 (example 24) to 100 (example 26) at a fixed L-LA/[LO$^1$]MgBu ratio of 5 000 and with the same reaction time, resulted in a slight decrease in activity; this presumably reflects the higher oxophilicity of Mg-based complexes in comparison with their zinc counterparts. This drop in kinetics could be partly circumvented by increasing the reaction temperature. Full conversion of 5 000 equivalents of L-LA could not however be achieved after 2 h as can be seen by comparing examples 25 and 27. Similarly, increasing monomer loadings while keeping the amount of transfer agent unchanged also led to a sizeable drop of activity as can be seen by comparing examples 24 and 28 and examples 27 and 29. This may be due to the exacerbated sensitivity of magnesium complexes towards the impurities present in the reaction mixture, despite a systematic, thorough purification of the monomer. Although slower kinetics were observed when increasing alcohol and/or L-LA contents, the molecular weights and their distribution were hardly modified by these processes, thereby suggesting that these phenomena were the result of partial catalyst de-activation with concomitant formation of species that were inert towards the monomer. It is believed that the presence of two active species would most likely result in a significant broadening of the polydispersity index contrary to what was observed here.

The complex [LO$^1$]MgBu exerted little stereo-control during the polymerisation of rac-LA in toluene as indicated in example 22 by a $P_m$ of 0.54. A slight propensity towards syndiotactic was however observed in THF as seen in example 23 with a Pm of 0.41. It must be noted that the stereo-selective nature of [LO$^1$]MgBu, although very limited, exerted itself in opposite ways in toluene where a preference for meso diads was observed and in THF where rac diads were favoured. The polymerisation kinetics and the quality of control exerted by the active species were virtually identical during the ROP of L-LA and rac-LA as can be seen by comparing examples 21 and 22.

A broad range of alcohol such as iPrOH, BnOH, TEMPO-OH, AA-OH, HEMA can be used as transfer agents, and a large variety of end-functionalised PLAs can thus be synthesised in the controlled, immortal ROP of LA promoted by [LO$^1$]MgBu.

A PLLA sample capped with an isopropoxy terminus was prepared by the immortal ROP of 5000 equiv. of L-LA with L-LA/[LO$^1$]MgBu/iPrOH in relative amounts of 5 000/1/100. The MALDI-TOF mass spectrum of the resulting low molecular weight PLLA, is displayed in FIG. 7(A). It demonstrates clearly that all polymer chains are terminated by a —OiPr moiety, which therefore represents conclusive evidence for the truly immortal nature of the ROP mechanism involved with this system. Increments of 72 Da between consecutive peaks throughout the whole Gaussian distribution showing two populations of uneven intensities, as seen in FIG. 7(B), indicate that trans-esterification processes occur to a considerable extent during the polymerisation of LA catalysed by such Mg complexes.

[LO$^1$]CaN(SiMe$_3$)$_2$.

The polymerisation conditions and results are summarised in Table IV.

TABLE IV

| Ex | Solvent | Alcohol | LA/Ca/ROH | [LA] mol/L | T (°C.) | t (min) | Yield (%) | $\overline{Mn}_{theo}$ (g/mol) | $\overline{Mn}_{GPC}$ (g/mol) | PDI | $P_m$ |
|---|---|---|---|---|---|---|---|---|---|---|---|
| 30 | toluene | — | L 500/1/0 | 2 | 60 | 1 | 8 | 5 800 | 8 300 | 1.43 | nd |
| 31 | toluene | iPrOH | L 500/1/1 | 2 | 60 | 5 | 51 | 36 800 | 28 400 | 1.38 | nd |
| 32 | toluene | iPrOH | L 500/1/5 | 2 | 60 | 1 | 83 | 12 000 | 11 800 | 1.38 | nd |
| 33 | toluene | iPrOH | L 500/1/10 | 2 | 60 | 1 | 94 | 6 800 | 6 500 | 1.27 | 1.00 |
| 34 | toluene | iPrOH | L 500/1/25 | 2 | 60 | 1 | 86 | 2 500 | 3 000 | 1.21 | nd |
| 35 | toluene | iPrOH | L 1 000/1/10 | 2 | 60 | 15 | 94 | 13 600 | 14 200 | 1.37 | nd |
| 36 | toluene | iPrOH | L 1 000/1/25 | 2 | 60 | 15 | 95 | 5 500 | 6 000 | 1.23 | nd |
| 37 | toluene | iPrOH | L 1 000/1/50 | 2 | 60 | 15 | 94 | 2 800 | 2 600 | 1.19 | nd |
| 38 | toluene | iPrOH | L 1 000/1/100 | 2 | 60 | 15 | 75 | 1 100 | 2 000 | 1.22 | nd |
| 39 | toluene | iPrOH | L 2 500/1/25 | 4 | 60 | 3 × 60 | 84 | 12 200 | 12 700 | 1.23 | nd |
| 40 | toluene | iPrOH | L 500/1/10 | 2 | 25 | 1 | 70 | 5 100 | 5 300 | 1.39 | Nd |
| 41 | toluene | iPrOH | Rac 500/1/10 | 2 | 60 | 2 | 78 | 5 700 | 5 300 | 1.39 | 0.50 |
| 42 | THF | iPrOH | Rac 1 000/1/10 | 2 | 60 | 15 | 30 | 4 400 | 5 400 | 1.29 | 0.50 |

The immortal polymerisation of LA was efficiently promoted by catalytic system [LO¹]CaN(SiMe₃)₂/ROH, in toluene or THF and wherein ROH was selected from iPrOH, BnOH, TEMPO-OH, AA-OH, HEMA. This represents the first example to date of a well-defined, heteroleptic phenoxy-based calcium complex, characterised both in solution and in the solid-state, capable of polymerising large quantities of monomer in a controlled fashion.

In absence of alcohol (example 30), initiator [LO¹]CaN(SiMe₃)₂ was rather slow in comparison to the other examples carried out in the presence of alcohol. In the presence of 10 to 100 equivalents of iPrOH, polymerisation of up to 2 500 equivalents of L-LA is achieved extremely rapidly at a temperature of 60° C. For instance, quantitative conversion of 500 equivalents of monomer was performed within one minute for ratio iPrOH/[LO¹]CaN(SiMe₃)₂>10 as seen in example 33. It took less than 15 min to convert 1 000 equivalents of monomer under the same conditions as shown in examples 35 to 37. Polymerisation was well controlled as indicated by polydispersity indexes in the range of 1.20 to 1.40, and by the close agreement between experimental and theoretical molecular weights, even for values of the ratio iPrOH/[LO¹]CaN(SiMe₃)₂ of 50. It must be mentioned that a significant broadening of the polydispersity index, which reached up to 1.6-1.7, was observed when the reactions were prolonged after complete conversion of the monomer, related to undesirable trans-esterification processes.

The catalyst [LO¹]CaN(SiMe₃)₂/iPrOH performed very well at low temperatures, both in terms of kinetics and of control. Thus, the conversion of 500 equivalents of monomer reached 70% after 1 minute at room temperature as seen in example 40 whereas it was complete at a temperature of 60° C. as shown in example 33.

The polymerisation of rac-LA in toluene (example 41) was significantly slower than that of L-LA (example 33) and not stereo-controlled with $P_m$=0.50. When carried out in THF (example 42), the polymerisation of rac-LA was comparatively even slower than in toluene and did not exhibit and stereo-selectivity with $P_m$=0.50.

Figure 8:
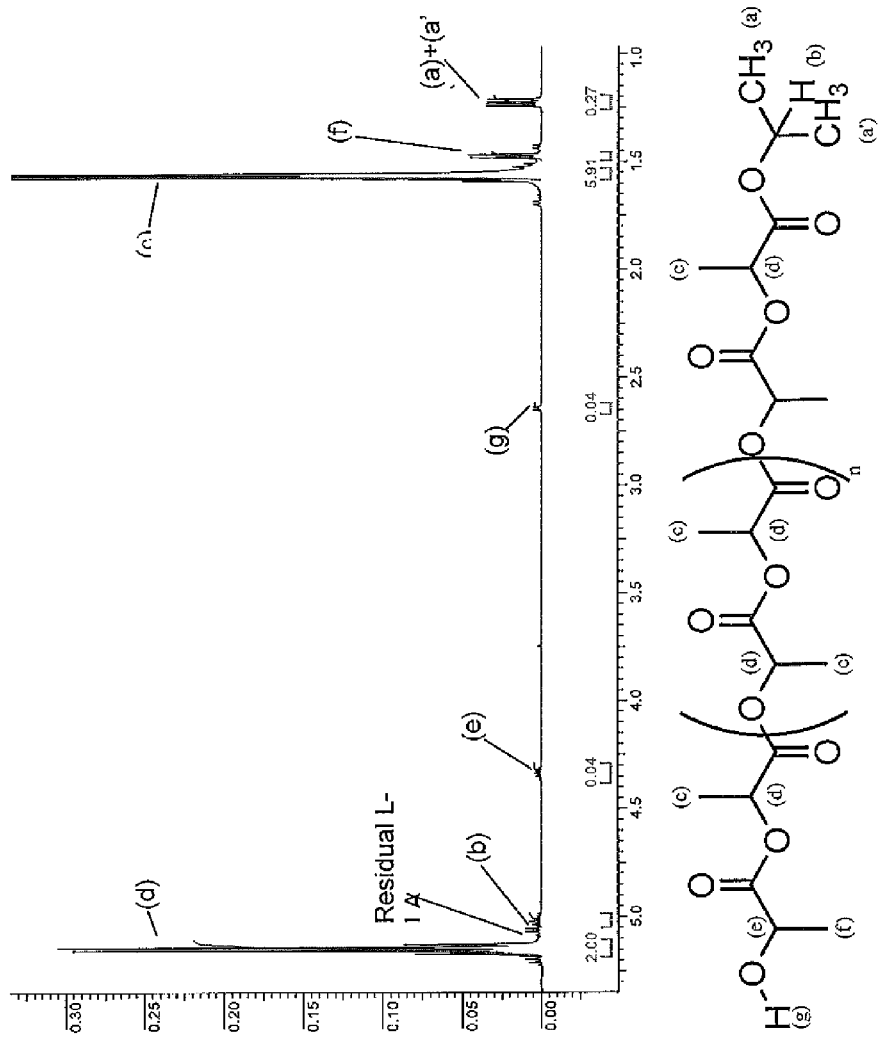
FIG. 8 represents the $^1$H NMR (500.13 MHz, CDCl$_3$, 25° C., 64 scans, D1=0.50 sec) spectrum of a low molecular weight PLLA ($\overline{Mn}_{GPC}$=3 000 g/mol, Table 4 entry 32) prepared with L-LA/[LO$^1$]CaN(SiMe$_3$)$_2$/iPrOH=500/1/25.
Figure 9A:
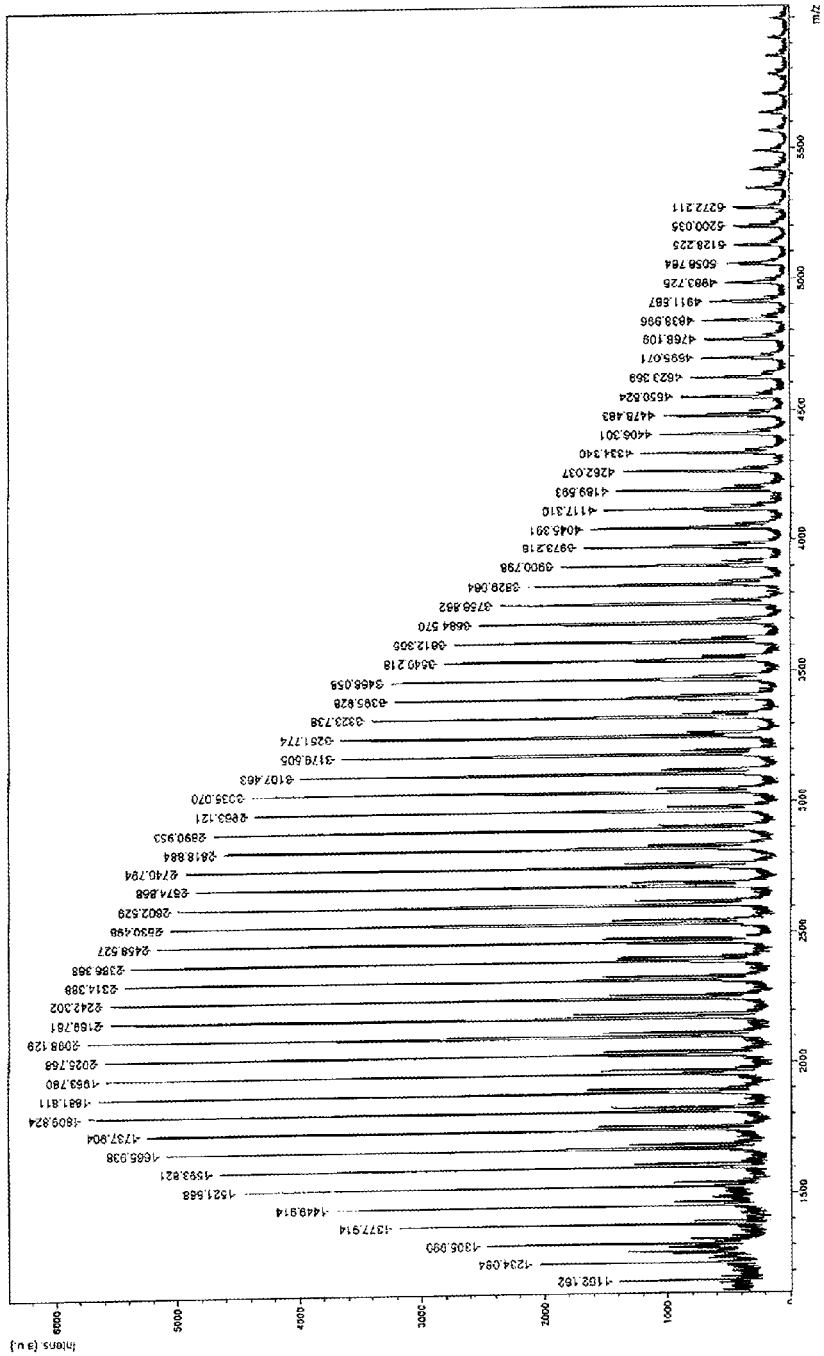
FIGS. 9A and 9B represent the MALDI-TOF mass spectrum (main population: Na$^+$; minor population: K$^+$) of a low molecular PLLA ($\overline{Mn}_{GPC}$=3 000 g/mol, Table 4 entry 34) prepared with L-LA/[LO$^1$]CaN(SiMe$_3$)$_2$/iPrOH=500/1/25 (conversion 86%, $\overline{Mn}_{theo}$=2 500 g/mol).
Figure 9B:
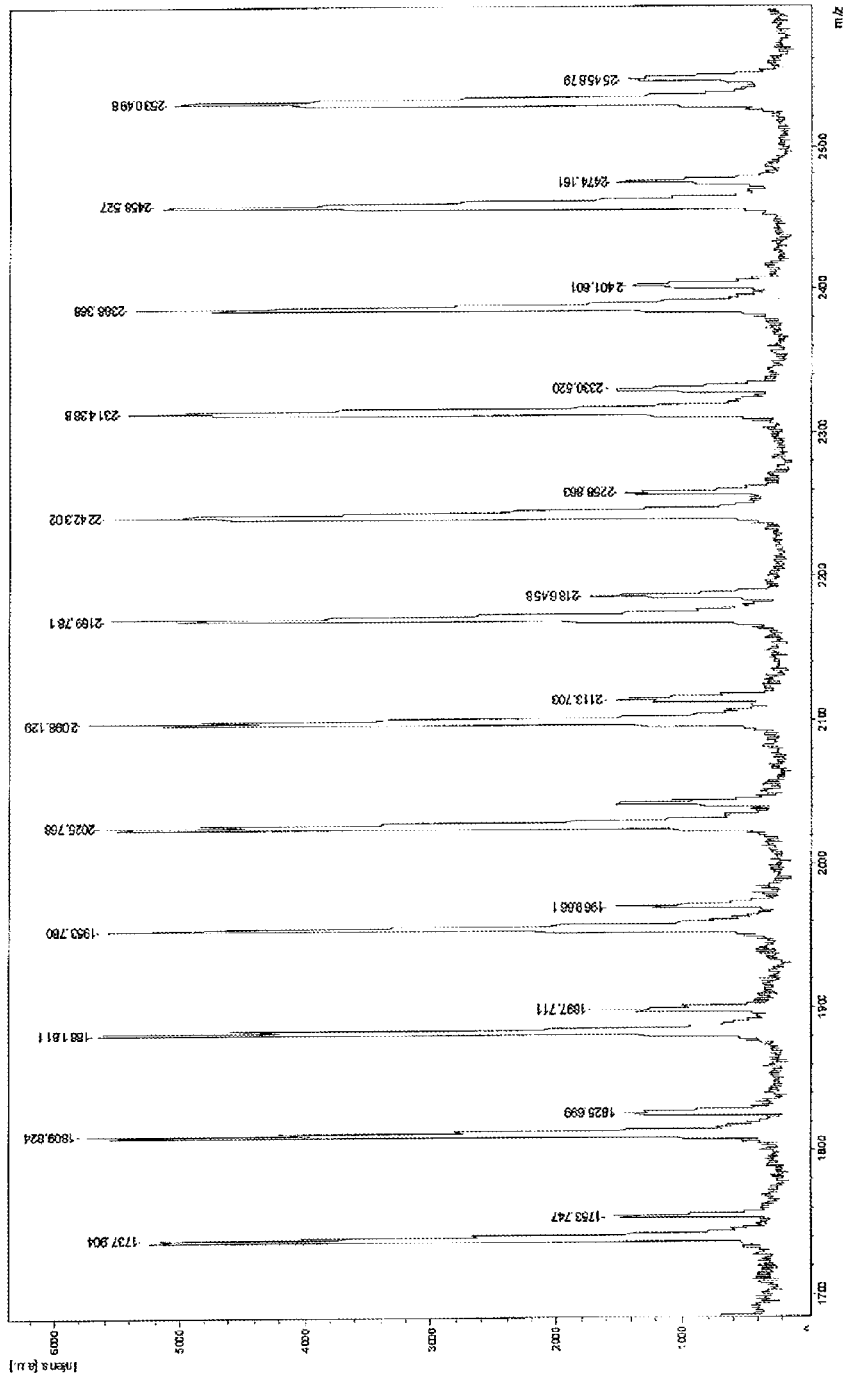

The nature of a single initiating group, namely, the isopropoxy group OCH(CH₃)₂— in the catalytic system [LO¹]CaN(SiMe₃)₂/iPrOH, was demonstrated by NMR spectroscopy and MALDI-TOF mass spectrometry. In the ¹H NMR spectrum of a low molecular weight PLLA, such as in example 34, prepared with L-LA/[LO¹]CaN(SiMe₃)₂/iPrOH in relative amounts of 500/1/25, the presence of —OCH(CH₃)₂ end-groups was identified by the characteristic signals at δ 5.06 (OCH(CH₃)₂) and 1.24 (OCH(CH₃)₂) ppm as shown in FIG. 8; there is no indication of the presence of PLLA chains initiated by either —N(SiMe₃)₂ or [LO¹]- groups. This analysis was further corroborated by inspection of the high resolution MALDI-TOF mass spectra of this PLLA sample as shown in FIGS. 9A-9B. There is a very good agreement between the theoretical molecular weights of isopropoxy-terminated PLLA chains and the GPC experimental results: two Gaussian distributions were observed (the first and second populations corresponding respectively to ionization with Na⁺ and K+[Δ(m/z)=16 Da between the two populations]) and the molecular weight of each peak was consistent with the calculated molecular weights for the on-matrix compounds (H)(C₆H₈O₄)ₙ(OiPr)(Na) and (H)(C₆H₈O₄)ₙ(OiPr)(K), where n is the degree of polymerisation. The fact that within a population (the main population corresponding to Na⁺) increments between consecutive peaks of only of 72 Da instead of the expected 144 Da constitute a strong evidence that undesirable trans-esterification reactions were promoted extremely rapidly by the calcium complex during the course of the polymerisation; this is consistent with earlier observations that the polydispersity index of PLLA broadened noticeably when the reaction was allowed to continue after full conversion of the monomer.

Comparison Between Initiators in Presence of iPrOH.

A series of experiments was conducted to determine the effectiveness of initiators, (BDI)ZnN(SiMe₃)₂, [LO¹]ZnEt, [LO²]ZnEt, [LO¹]MgBu and [LO¹]CaN(SiMe₃)₂ for the immortal ROP of large quantities of L-LA with iPrOH in toluene. The polymerisation conditions and results are reported in Table V.

TABLE V

| Ex | Initiator | LA/[M]/iPrOH | [LA] (mol/L) | T (° C.) | t (min) | Yield (%) | $\overline{Mn}_{theo}$ (g/mol) | $\overline{Mn}_{GPC}$ (g/mol) | PDI |
|---|---|---|---|---|---|---|---|---|---|
| 43 | (BDI)ZnN(SiMe$_3$)$_2$ | L 1 000/1/10 | 2 | 60 | 15 | 84 | 12 100 | 15 500 | 1.07 |
| 44 | [LO$^1$]ZnEt | L 1 000/1/10 | 2 | 60 | 15 | 20 | 2 900 | 4 700 | 1.09 |
| 45 | [LO$^2$]ZnEt | L 1 000/1/10 | 2 | 60 | 15 | 0 | — | — | — |
| 46 | [LO$^1$]MgBu | L 1 000/1/10 | 2 | 60 | 15 | 95 | 13 700 | 15 300 | 1.14 |
| 47 | [LO$^1$]CaN(SiMe$_3$)$_2$ | L 1 000/1/10 | 2 | 60 | 15 | 84 | 12 100 | 15 600 | 1.27 |
| 48 | [LO$^1$]ZnEt | L 5 000/1/25 | 4 | 60 | 60 | 71 | 20 500 | 20 600 | 1.09 |
| 49 | [LO$^2$]ZnEt | L 5 000/1/25 | 4 | 60 | 60 | 45 | 13 000 | 13 000 | 1.09 |
| 50 | (BDI)ZnN(SiMe$_3$)$_2$ | L 5 000/1/25 | 4 | 60 | 60 | 95 | 27 400 | 26 900 | 1.13 |
| 51 | [LO$^1$]ZnEt | L 5 000/1/25 | 4 | 60 | 90 | 94 | 27 100 | 26 200 | 1.16 |
| 52 | [LO$^2$]ZnEt | L 5 000/1/25 | 4 | 60 | 90 | 92 | 26 500 | 26 300 | 1.12 |
| 53 | (BDI)ZnN(SiMe$_3$)$_2$ | L 5 000/1/25 | 4 | 60 | 90 | 96 | 27 700 | 28 500 | 1.14 |
| 54 | [LO$^1$]MgBu | L 5 000/1/25 | 4 | 4 | 60 | 79 | 22 700 | 20 500 | 1.14 |
| 55 | [LO$^1$]ZnEt | L 20 000/1/100 | 6 | 60 | 4 × 60 | 95 | 27 400 | 26 300 | 1.28 |
| 56 | (BDI)ZnN(SiMe$_3$)$_2$ | L 20 000/1/100 | 6 | 60 | 4 × 60 | 82 | 23 600 | 22 000 | 1.24 |
| 57 | [LO$^1$]ZnEt | L 20 000/1/250 | 6 | 60 | 78 | 74 | 8 500 | 8 900 | 1.16 |
| 57bis | ZnEt$_2$ | L 20 000/1/250 | 6 | 60 | 78 | 11 | 1 300 | 1 600 | 1.09 |
| 58 | (BDI)ZnN(SiMe$_3$)$_2$ | L 20 000/1/250 | 6 | 60 | 78 | 65 | 7 500 | 6 700 | 1.10 |
| 59 | [LO$^1$]ZnEt | L 50000/1/250 | 6 | 60 | 8 × 60 | 86 | 24 800 | 17 700 | 1.43 |
| 60 | [LO$^1$]ZnEt | L 50000/1/500 | 6 | 60 | 16 × 60 | 100 | 14 500 | 13 500 | 1.60 |

For all the tested metallic initiators, the control of the polymerisation parameters was always good to excellent as indicated in Table V by narrow polydispersity index and good agreement between theoretical and observed molecular weights. The comparison between catalytic systems is therefore solely based here on polymerisation kinetics.

Examples 43 to 47 performed with a ratio L-LA/[M]/iPrOH of 1 000/1/10 at a temperature of 60° C. and for a period of time of 15 minutes indicated that complexes [LO$^1$]ZnEt and [LO$^2$]ZnEt seemed far less active than the other 3 precursors, and they were ranked as follows in terms of increasing activity: [LO$^2$]ZnEt<<[LO$^2$]ZnEt<<(BDI)ZnN(SiMe$_3$)$_2$=[LO$^1$]CaN(SiMe$_3$)$_2$<[LO$^1$]MgBu. It is postulated that the lack of efficiency displayed by [LO$^1$]ZnEt and [LO$^2$]ZnEt under such conditions and short reaction times reflects the fact that the catalysts based on these two precursors require an activation period of 10 to 15 minutes as was observed in Tables I and 11.

At longer reaction times and higher monomer loadings, the order of efficiency was different. For example, for L-LA/[M]/iPrOH of 5 000/1/25 at a temperature of 60° C. for a period of time of 90 minutes, the order of efficiency was [LO$^1$]MgBu< [LO$^1$]ZnEt~[LO$^2$]ZnEt~(BDI)ZnN(SiMe$_3$)$_2$. Full conversion was achieved with the zinc complexes, while it was below 80% with [LO$^1$]MgBu. This reflects the characteristic higher sensitivity of Mg-based complexes with respect to their Zn-based analogues.

To further discriminate between the three Zn-based catalytic systems, the reaction were deliberately quenched after 60 minutes, before complete conversion of the monomer was achieved with all 3 catalysts, and the following results were observed: [LO$^2$]ZnEt (45%)<[LO$^1$]ZnEt (71%)<(BDI)ZnN(SiMe$_3$)$_2$ (95%). This is shown in examples 48 to 50.

It can be concluded that:
1—For the immortal ROP of large quantities of LA of several dozen thousands of equivalents, with up to 100 to 500 equivalents of transfer agent, the best candidates are the Zn-based initiators;
2—Under identical conditions, [LO$^1$]ZnEt is more efficient than [LO$^2$]ZnEt;
3—The detrimental effect, in terms of polymerisation kinetics, of the induction period required for activating [LO$^1$]ZnEt (and [LO$^2$]ZnEt) is negligible at reaction times larger than 90 minutes.

A second series of experiments was carried out, focusing on [LO$^1$]ZnEt, that was the most promising initiator, and (BDI)ZnN(SiMe$_3$)$_2$ in order to perform the immortal ROP of L-LA under industrially relevant experimental conditions as presented in examples 55 to 60. Both sets of experiments were carried out respectively with 100 equivalents (examples 55 and 56) and 250 equivalents of alcohol (examples 57, 57bis, 58 and 59) for the polymerisation of 20 000 equivalents of monomer. The results indicate that under such conditions, the order of activity is reversed: (BDI)ZnN(SiMe$_3$)$_2$<[LO$^1$]ZnEt; both were far superior to the simple ZnEt$_2$ precursor of example 57bis.

Quite surprisingly, the immortal ROP of 50 000 equiv. of L-LA with [LO$^1$]ZnEt/iPrOH=1/250 at 60° C. was still very well controlled and nearly quantitative within as little as 8 h (entry 59), while complete conversion was achieved after 16 hours in presence of as much as 500 equiv. of alcohol (entry 60). The scope offered by complex [LO$^1$]ZnEt for the ROP of LA is great, as there is currently no indication that the maximal performances have been achieved yet with this system.

Polymerisation of Lactide in Styrene.

The reaction steps are represented in scheme 5 and the polymerisation conditions and results are presented in Table VI.

Table VI. For instance, polymerisation of 1 000 equivalents of L-LA in styrene was completed in less than 15 minutes, well controlled, and proceeded without interference and without polymerisation of styrene. This therefore makes these systems suitable for the large-scale synthesis of terminally functionalised PLLA and subsequent preparation of poly(LA-block-styrene) copolymers.

Bulk Polymerization of Trimethylene Carbonate (TMC) in Presence of Benzyl Alcohol.

The reaction steps are represented in scheme 6 and the polymerisation conditions and results are presented in Table VII.

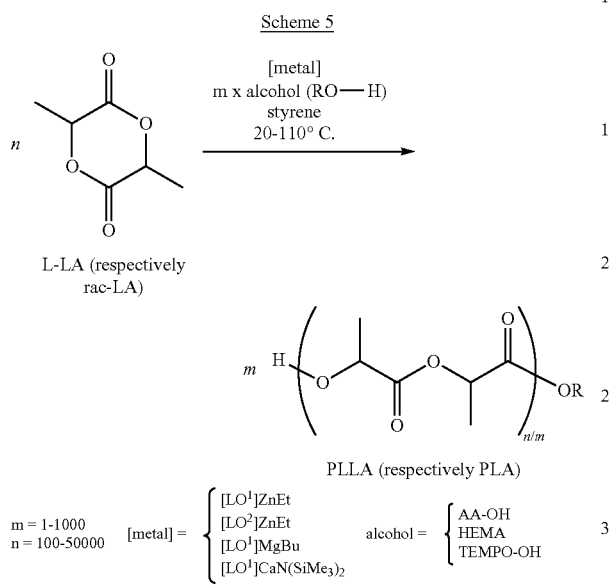

Scheme 5

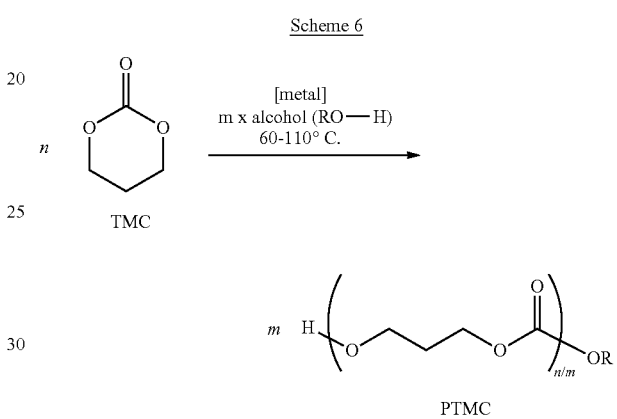

Scheme 6

TABLE VI

| Ex | Initiator | LA/[M]/TEMPO-OH | [LA] (mol/L) | T (° C.) | t (min) | Yield (%) | $\overline{M}n_{theo}$ (g/mol) | $\overline{M}n_{GPC}$ (g/mol) | PDI |
|---|---|---|---|---|---|---|---|---|---|
| 61 | [LO$^1$]ZnEt | L 1 000/1/5 | 2 | 100 | 30 | 99 | 28 700 | 24 800 | 1.50 |
| 62 | [LO$^1$]ZnEt | L 1 000/1/10 | 2 | 100 | 30 | 98 | 14 300 | 14 900 | 1.43 |
| 63 | [LO$^1$]ZnEt | L 1 000/1/10 | 4 | 100 | 15 | 99 | 14 400 | 13 700 | 1.30 |
| 64 | [LO$^1$]MgBu | L 1 000/1/10 | 2 | 100 | 15 | 97 | 14 100 | 12 900 | 1.17 |

In this Table, the theoretical value of Mn is calculated from [LA]$_0$/[ROH]$_0$×monomer conversion×ML$_A$+M$_{TEMPO-OH}$, wherein ML$_A$=144 g/mol and M$_{TEMPO-OH}$=162 g/mol.

In association with a broad range of transfer agents selected from iPrOH, BnOH, TEMPO-OH, AA-OH, HEMA, the metallic initiators of the present invention were suitable for the immortal ROP of LA in styrene, as exemplified in

TABLE VII

| Ex | Initiator | TMC/[Zn]/BnOH | T (° C.) | t (min) | Yield (%) | $\overline{M}n_{theo}$ (g/mol) | $\overline{M}n_{GP}{}^c$ (g/mol) | PDI |
|---|---|---|---|---|---|---|---|---|
| 65 | (BDI)ZnN(SiMe$_3$)$_2$ | 500/1/5 | 60 | 7 | 99 | 10 200 | 12 400 | 1.55 |
| 66 | [LO$^1$]ZnEt | 500/1/5 | 60 | 7 | 98 | 10 100 | 12 100 | 1.52 |
| 67 | (BDI)ZnN(SiMe$_3$)$_2$ | 10 000/1/20 | 60 | 3 × 60 | 89 | 45 500 | 43 300 | 1.90 |
| 68 | [LO$^1$]ZnEt | 10 000/1/20 | 60 | 3 × 60 | 100 | 51 100 | 49 200 | 1.54 |
| 69 | (BDI)ZnN(SiMe$_3$)$_2$ | 25 000/1/20 | 60 | 15 × 60 | 75 | 95 800 | 93 400 | 1.65 |
| 70 | [LO$^1$]ZnEt | 25 000/1/20 | 60 | 15 × 60 | 97 | 123 900 | 117 200 | 1.62 |
| 71 | [LO$^1$]ZnEt | 100 000/1/100 | 60 | 48 × 60 | 93 | 95 000 | 88 700 | 1.61 |
| 72 | [LO$^1$]ZnEt | 100 000/1/100 | 110 | 8 × 60 | 96 | 98 000 | 94 400 | 1.51 |

In this Table, the theoretical value of Mn is calculated from $[LA]_0/[ROH]_0 \times$ monomer conversion $\times ML_A + M_{TEMPO-OH}$, wherein $ML_A = 144$ g/mol and $M_{BnOH} = 162$ g/mol.

Upon addition of a transfer agent selected from iPrOH, BnOH, TEMPO-OH, AA-OH, or HEMA, all metallic complexes according to the present invention made suitable catalysts for the immortal ROP of TMC carried out in bulk monomer.

$$m = 1\text{-}1000 \quad n = 100\text{-}100000 \quad [\text{metal}] = \begin{cases} [LO^1]ZnEt \\ [LO^2]ZnEt \\ [LO^1]MgBu \\ [LO^1]CaN(SiMe_3)_2 \end{cases} \quad \text{alcohol} = \begin{cases} AA\text{-}OH \\ HEMA \\ TEMPO\text{-}OH \end{cases}$$

TABLE VIII

| Ex | Initiator | ROH | TMC/[M]/ROH | t (min) | Yield (%) | $\overline{Mn}_{theo}$ (g/mol) | $\overline{Mn}_{GPC}$ (g/mol) | PDI |
|---|---|---|---|---|---|---|---|---|
| 73 | (BDI)ZnN(SiMe$_3$)$_2$ | iPrOH | 5 000/1/20 | 60 | 99 | 25 800 | 27600 | 1.8 |
| 74 | (BDI)ZnN(SiMe$_3$)$_2$ | TEMPO-OH | 5 000/1/20 | 60 | 98 | 25 600 | 25 500 | 1.9 |
| 75 | (BDI)ZnN(SiMe$_3$)$_2$ | AA-OH | 5 000/1/20 | 60 | 99 | 25 900 | 25 100 | 1.8 |
| 76 | [LO$^1$]ZnEt | AA-OH | 5 000/1/20 | 60 | 80 | 20 400 | 17 400 | 1.6 |

For instance, upon addition of 5 to 20 equivalents of benzylic alcohol, [LO$^1$]ZnEt afforded the complete conversion of up to 25 000 equivalents of TMC within a few hours at a temperature of 60° C. as seen in examples 66, 68 and 70. Polydispersity index of 1.50 to 1.65 were typical of this type of zinc-promoted ROP of TMC, and the correlation between observed and calculated molecular weights was very good.

In terms of control, activity and productivity, [LO$^1$]ZnEt compared favourably with (BDI)ZnN(SiMe$_3$)$_2$, the former allowing full conversion of 10 000 or 25 000 equivalents of TMC as shown in examples 68 and 70 whereas the latter only converted respectively 89% and 75% of the monomer as seen in examples 67 and 69. This made the binary system [LO$^1$]ZnEt/BnOH the most active and productive catalytic system for the immortal ROP of TMC, outclassing the system (BDI)ZnN(SiMe$_3$)$_2$/BnOH previously described in patent application EP-08 290 187.7 In addition, the new [LO$^1$]ZnEt/BnOH catalyst also offered a better control of the polymerisation as indicated by narrow PDI and better match between experimental and theoretical values of Mn.

Surprisingly, nearly complete conversion of up to 100 000 equiv. of TMC was achieved within 48 h at a temperature of 60° C. upon addition of 100 equivalents of BnOH as shown in example 71. The resulting polymer displayed a narrow PDI and the experimental molecular weights remained in complete agreement with its calculated value. Upon heating to 110° C., the reaction time was conveniently cut down to 8 h with no obvious detrimental effect as seen in example 72.

Polymerisation of Trimethylene Carbonate (TMC) in Styrene.

The reaction steps are represented in scheme 7 and the polymerisation conditions and results are presented in Table VIII.

TMC was polymerised in styrene without any noticeable detrimental effect from the solvent in a controlled, immortal manner with an initiator selected from (BDI)Zn—N(SiMe$_3$)$_2$, [LO$^1$]ZnEt, [LO$^2$]ZnEt, [LO$^1$]MgBu or [LO$^1$]CaN(SiMe$_3$)$_2$ and an alcohol selected from iPrOH, BnOH, AA-OH, HEMA and TEMPO-OH.

Complete conversion of 5 000 equivalents of TMC and good agreement between theoretical and experimental molecular weights were observed, although the polydispersity index, typically of 1.8 to 1.9 was larger than those observed for the ROP of LA that were typically of 1.20 to 1.40 under similar conditions.

Bulk Polymerization of Various 6-Membered Carbonates in Presence of Benzyl Alcohol.

The reaction steps are represented in scheme 8 and the polymerisation conditions and results are presented in Table IX

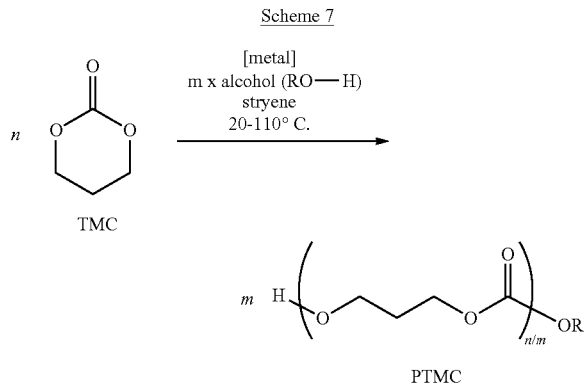

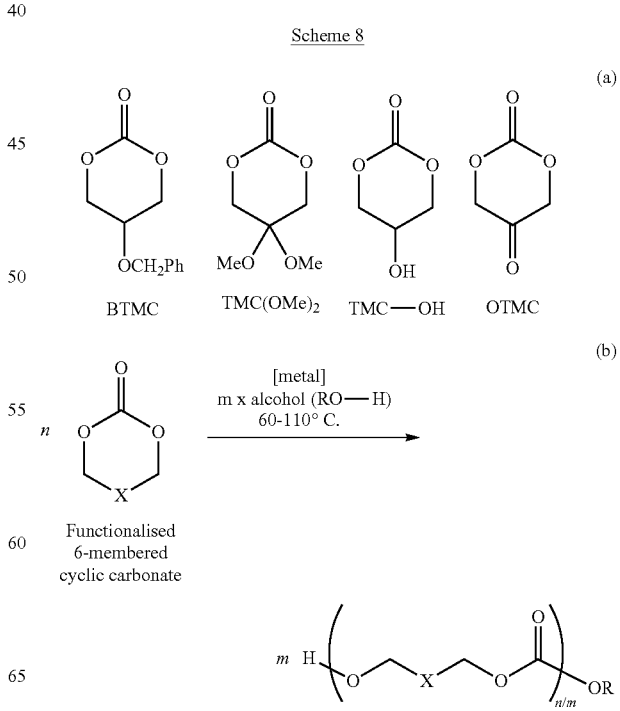

-continued m = 1-100    X = CH(CH₂Ph), BTMC
n = 100-10000    X = C(OMe)₂, TMC(OMe)₂    [metal] = { [LO¹]ZnEt, [LO²]ZnEt, [LO¹]MgBu, [LO¹]CaN(SiMe₃)₂ }
X = CH(OH), TMC-OH
X = C(O), OTMC alcohol = { 2-propanol, benzyl alcohol, AA-OH, HEMA, TEMPO-OH }

Functionalised 6-membered cyclic carbonates were polymerised in bulk in a controlled, immortal manner with an initiator selected from (BDI)Zn—N(SiMe₃)₂, [LO¹]ZnEt, [LO²]ZnEt, [LO¹]MgBu or [LO¹]CaN(SiMe₃)₂ and an alcohol selected from iPrOH, BnOH, AA-OH, HEMA and TEMPO-OH, as shown in Table IX.

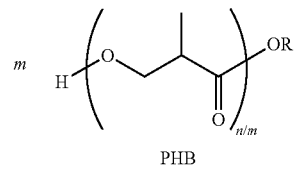

PHB m = 1-100
n = 100-10000    [metal] = { [LO¹]ZnEt, [LO²]ZnEt, [LO¹]MgBu, [LO¹]CaN(SiMe₃)₂ }    alcohol = { 2-propanol, benzyl alcohol, AA-OH, HEMA, TEMPO-OH }

TABLE IX

| Ex | Initiator | Monomer | [Mon.]/[M]/ROH | T (°C.) | t (min) | Yield (%) | $\overline{Mn}_{theo}$ (g/mol) | $\overline{Mn}_{GPC}$ (g/mol) | PDI |
|---|---|---|---|---|---|---|---|---|---|
| 77 | (BDI)ZnN(SiMe₃)₂ | TMC(OMe)₂ | 500/1/5 | 90 | 60 | 93 | 15 200 | 17 000 | 1.25 |
| 78 | [LO¹]ZnEt | TMC(OMe)₂ | 500/1/5 | 90 | 15 | 96 | 15 700 | 15 000 | 1.47 |
| 79 | (BDI)ZnN(SiMe₃)₂ | BTMC | 500/1/5 | 90 | 30 | 100 | 20 900 | 13 500 | 1.61 |
| 80 | [LO¹]ZnEt | BTMC | 500/1/5 | 90 | 30 | 100 | 20 900 | 13 200 | 1.62 |

In the presence of 5 equivalents of transfer agent, complete conversion of 500 equivalents of monomer was observed

TABLE X

| Ex | Initiator | BBL/[Zn]/iPrOH | T (°C.) | t (min) | Yield (%) | $\overline{Mn}_{theo}$ (g/mol) | $\overline{Mn}_{GPC}$ (g/mol) | PDI | $\overline{Mn}_{MALDI}$ (g/mol) |
|---|---|---|---|---|---|---|---|---|---|
| 81 | [LO¹]ZnEt | 200/1/10 | 60 | 60 | 95 | 2 000 | 1 700 | 1.11 | 2 000 |
| 82 | [LO¹]ZnEt | 500/1/10 | 60 | 3 × 60 | 95 | 4 100 | 4 300 | 1.07 | 4 000 |
| 82bis | [LO¹]ZnEt | 750/1/10 | 60 | 4 × 60 | 84 | 5 400 | 6 400 | 1.10 | n.d. |
| 83 | [LO¹]ZnEt | 1 000/1/10 | 60 | 4 × 60 | 77 | 7 000 | 7 500 | 1.07 | 6 500 |
| 84 | [LO¹]ZnEt | 1 000/1/10 | 60 | 8 × 60 | 79 | 6 800 | 8 300 | 1.11 | n.d. |
| 85 | (BDI)ZnN(SiMe₃)₂ | 1 000/1/10 | 60 | 8 × 60 | 67 | 5 800 | 6 800 | 1.11 | n.d. |
| 86 | [LO¹]ZnEt | 2 000/1/25 | 60 | o/n | 40 | n.d. | n.d. | n.d. | n.d. | within 15 to 60 min. The polydispersity index, typically of 1.20 to 1.70, was narrow, and the observed molecular weights were close to their calculated values. Mark-Houwink coefficient was not applied here for the correction of the molecular weights which were directly given vs. polystyrene standards.

Polymerisation of Racemic β-Butyrolactone.

The reaction steps are represented in scheme 9 and the polymerisation conditions and results are presented in Table X.

Scheme 9

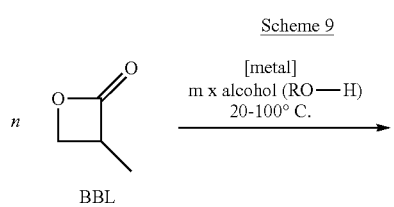

BBL

[metal]
m x alcohol (RO—H)
20-100° C.

The bulk polymerisation of rac-BBL was efficiently promoted in a controlled, immortal manner with an initiator selected from (BDI)Zn—N(SiMe₃)₂, [LO¹]ZnEt, [LO²]ZnEt, [LO¹]MgBu or [LO¹]CaN(SiMe₃)₂ and an alcohol detected from iPrOH, BnOH, AA-OH, HEMA and TEMPO-OH, as seen in Table X.

Upon addition of 10 equivalents of iPrOH, [LO¹]ZnEt readily converted 200 to 500 equivalents of rac-BBL within hours in a quantitative fashion. The PDI of the resulting polymers were very narrow, typically around 1.10, and the experimental molecular weights (determined by GPC or MALDI-TOF mass spectroscopy) were in excellent agreement with their theoretical values. [LO¹]ZnEt compared well with prior art (BDI)Zn—N(SiMe₃)₂, both in terms of activity and control, as shown by examples 84 and 85.

What is claimed:
1. A process comprising: controlled immortal ring-opening polymerisation of lactides, cyclic esters, 5-membered cyclic carbonates, 6-membered cyclic carbonates or 7-membered cyclic carbonates in the presence of a system comprising a complex of a divalent metal supported chelating phenoxy ligand and an alcohol or poly-ol;
wherein the complex of the divalent metal is of formula [LO]-M-X, wherein M is selected from Group 2 or 12 of the Periodic Table; wherein X is hydrocarbyl, or alkoxide group OR", wherein R" is hydrocarbyl, aryl, silyl, or amino group NR*$_2$, wherein R* is SiMe$_3$, iso-propyl, methyl or ethyl, and wherein [LO] is represented by formula:

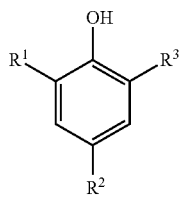

wherein R$^1$ is

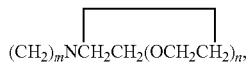

wherein m is 1, 2 or 3 and n≥1;
wherein R$^2$ is hydrocarbyl group having 1 to 10 carbon atoms; and
wherein R$^3$ is the same as R$^1$ or is hydrocarbyl group having 1 to 20 carbon atoms.

2. The process of claim 1, wherein an amount of the alcohol or the poly-ol is of from 1 to 10,000 equivalents per the divalent metal.

3. The process of claim 1, wherein the system comprises the alcohol, wherein the alcohol is R'OH, and wherein R' is a primary or secondary alkyl residue or benzylic group.

4. The process of claim 1, wherein the cyclic esters are selected from L-lactide (L-LA), rac-lactide (rac-LA), or rac-β-butyrolactone (rac-BBL) and the cyclic carbonates are selected from TMC and its substituted derivatives:

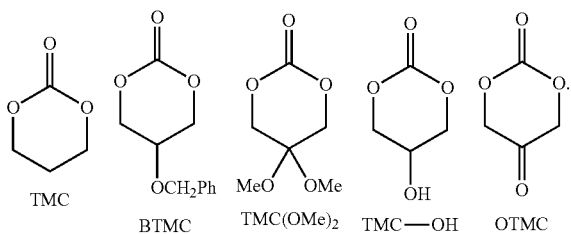

5. The process of claim 1, wherein the system comprises the alcohol, wherein the alcohol is functionalized, and wherein the ring-opening polymerisation is carried out in styrene in order to prepare end-functionalised polymers.

6. The process of claim 5, wherein the functionalised alcohol is selected from TEMPO-OH, HEMA or hydroxyalkoxyamines.

7. The process of claim 5, further comprising using the end-functionalised polymers to prepare in situ copolymers of lactide or TMC and styrene.

8. Polymers or copolymers obtained by the process of claim 1.

9. The polymers or copolymers of claim 8, wherein the polymers or copolymers exhibit a unimodal molecular weight distribution ranging from 1.1 to 5.0.

10. The polymers or copolymers of claim 8, wherein the polymers or copolymers exhibit a number average molecular weight M$_n$ ranging from 1,000 to 1,000,000 g/mol.

11. Copolymers obtained by the process of claim 7.

12. The process of claim 1, further comprising, prior to the ring-opening polymerization, preparing the complex of the divalent metal by reacting precursor MX$_2$ with pro-ligand of formula:

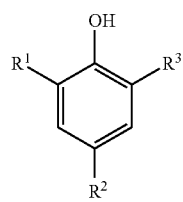

wherein M, X, R$^1$, R$^2$ and R$^3$ are as defined in claim 1.

13. The process of claim 1, wherein the ring-opening polymerization is carried out in solution in an organic solvent.

14. The process of claim 1, wherein the ring-opening polymerization is carried out in melt in the absence of solvent.

15. The process of claim 1, wherein the ring-opening polymerization is carried out at a temperature ranging from 20° C. to 200° C.

16. The process of claim 1, wherein the ring-opening polymerization is carried out at a pressure ranging from 0.5 to 20 atm.

17. The process of claim 1, wherein R$^2$ is selected from methyl, ethyl, iso-propyl, tert-butyl and neo-pentyl; and
wherein R$^3$ is an alkyl selected from methyl, ethyl, iso-propyl, tert-butyl, neo-pentyl, cumyl, and trityl, or an aryl selected from phenyl, 2,4,6-trimethylphenyl, and 2,6-diisopropylphenyl.

18. The process of claim 1, wherein R$^2$ is selected from methyl, ethyl, iso-propyl, tert-butyl and neo-pentyl; and
wherein R$^3$ is the same as R$^1$.

19. The process of claim 1, wherein the metal M is selected from Zn, Mg, Ca, Sr or Ba.

20. The process of claim 1, wherein X is selected from methyl, ethyl, n-butyl, phenyl, an amido group, or an alkoxide group.

* * * * *